United States Patent
Wakai et al.

(10) Patent No.: US 9,878,449 B2
(45) Date of Patent: Jan. 30, 2018

(54) MANIPULATOR SYSTEM

(71) Applicant: OLYMPUS CORPORATION, Tokyo (JP)

(72) Inventors: Hiroshi Wakai, Tokyo (JP); Naoya Hatakeyama, Tokyo (JP); Masatoshi Iida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 203 days.

(21) Appl. No.: 15/002,721

(22) Filed: Jan. 21, 2016

(65) Prior Publication Data

US 2016/0136810 A1 May 19, 2016

Related U.S. Application Data

(63) Continuation of application No. PCT/JP2014/069261, filed on Jul. 18, 2014.

(30) Foreign Application Priority Data

Jul. 25, 2013 (JP) ................................ 2013-154467

(51) Int. Cl.
*G06F 19/00* (2011.01)
*B25J 9/16* (2006.01)
(Continued)

(52) U.S. Cl.
CPC ......... *B25J 9/1635* (2013.01); *A61B 1/00059* (2013.01); *A61B 1/00133* (2013.01);
(Continued)

(58) Field of Classification Search
None
See application file for complete search history.

(56) References Cited

U.S. PATENT DOCUMENTS

| 2007/0078301 A1 | 4/2007 | Kura et al. |
| 2009/0143642 A1 | 6/2009 | Takahashi et al. |
| 2009/0149711 A1 | 6/2009 | Tanaka et al. |

FOREIGN PATENT DOCUMENTS

| EP | 2 038 712 B1 | 8/2011 |
| JP | 2000-126120 A | 5/2000 |

(Continued)

OTHER PUBLICATIONS

International Search Report dated Oct. 7, 2014 issued in PCT/JP2014/069261.

*Primary Examiner* — Bhavesh V Amin
(74) *Attorney, Agent, or Firm* — Scully, Scott, Murphy & Presser, P.C.

(57) ABSTRACT

Provided is a manipulator system including: a manipulator that has an insertion section composed of a flexible section and a bending section and that has a bending-section drive unit for driving the bending section; an operation input unit; a flexible-section shape detecting unit and a bending-section shape detecting unit that detect curved shapes of the flexible section and the bending section, respectively; compensation-value setting units that set a compensation value on the basis of the curved shape detected by each of the shape detecting units; and a control unit that generates a curvature control signal for driving the bending-section drive unit according to an operating instruction input via the operation input unit and furthermore corrects the curvature control signal using the compensation value and transmits it to the bending-section drive unit.

14 Claims, 18 Drawing Sheets

(51) Int. Cl.
  *B25J 18/06*  (2006.01)
  *A61B 90/96*  (2016.01)
  *A61B 1/00*  (2006.01)
  *B25J 13/06*  (2006.01)
  *A61B 34/30*  (2016.01)
  *A61B 34/37*  (2016.01)
  *A61B 90/98*  (2016.01)
  *A61B 34/20*  (2016.01)
  *G02B 23/24*  (2006.01)
  *A61B 17/00*  (2006.01)

(52) U.S. Cl.
  CPC .............. *A61B 34/30* (2016.02); *A61B 34/37* (2016.02); *A61B 90/96* (2016.02); *A61B 90/98* (2016.02); *B25J 9/1638* (2013.01); *B25J 9/1689* (2013.01); *B25J 13/06* (2013.01); *B25J 18/06* (2013.01); *A61B 2017/00022* (2013.01); *A61B 2017/0034* (2013.01); *A61B 2034/2051* (2016.02); *A61B 2034/2061* (2016.02); *A61B 2034/301* (2016.02); *G02B 23/2476* (2013.01); *G05B 2219/40279* (2013.01); *Y10S 901/09* (2013.01)

(56) References Cited

FOREIGN PATENT DOCUMENTS

| | | |
|---|---|---|
| JP | 2001-258828 A | 9/2001 |
| JP | 2002-264048 A | 9/2002 |
| JP | 2003-164420 A | 6/2003 |
| JP | 2007-089808 A | 4/2007 |
| JP | 2007-283115 A | 11/2007 |
| JP | 2009-000500 A | 1/2009 |
| JP | 2009-131374 A | 6/2009 |
| JP | 2009-131406 A | 6/2009 |
| JP | 2009-136618 A | 6/2009 |
| JP | 2009-273890 A | 11/2009 |
| JP | 2009-539573 A | 11/2009 |
| JP | 2010-214128 A | 9/2010 |
| JP | 5048158 B2 | 10/2012 |

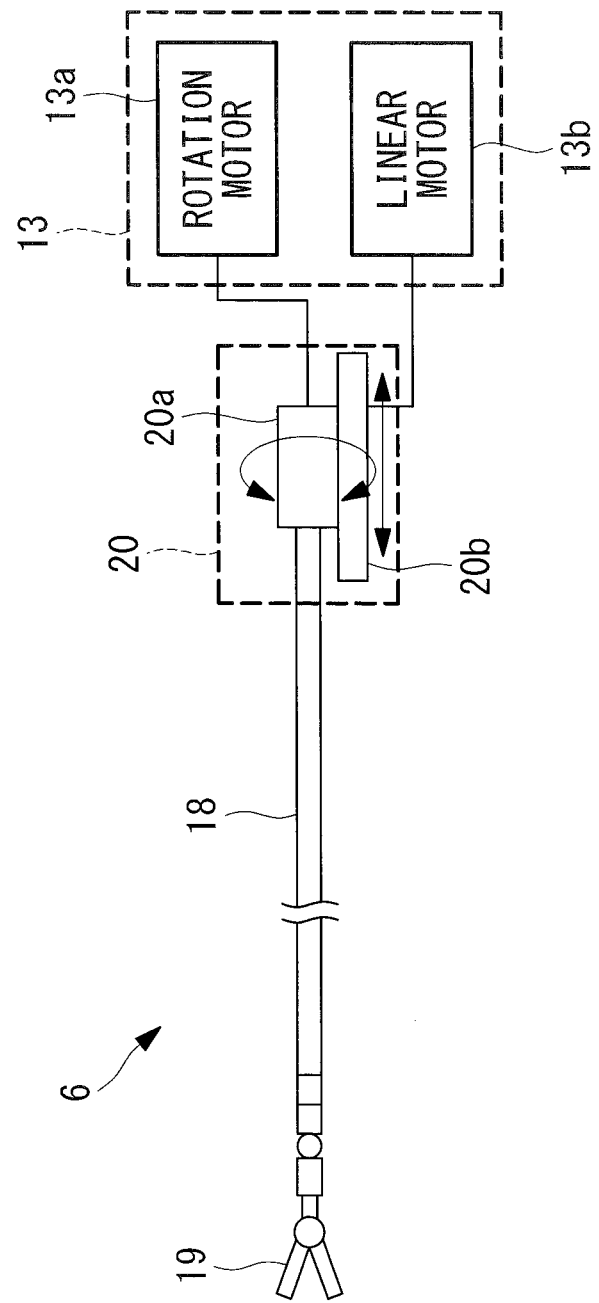

FIG. 15A
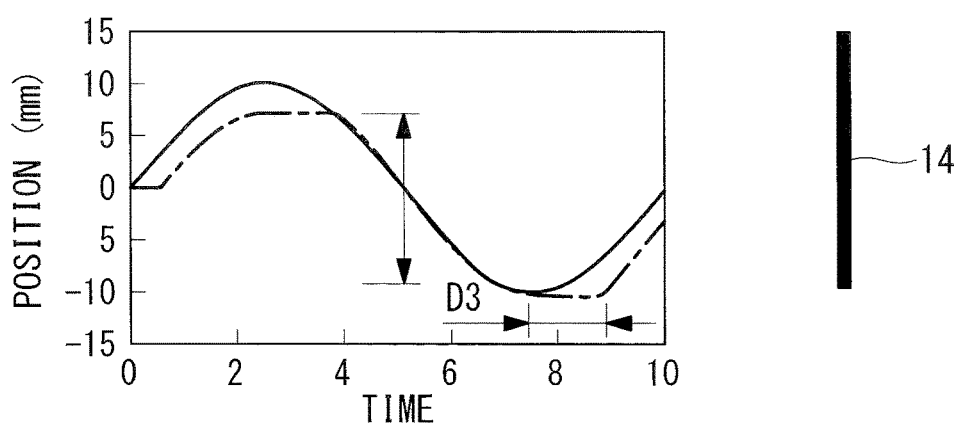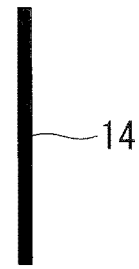
FIG. 15B
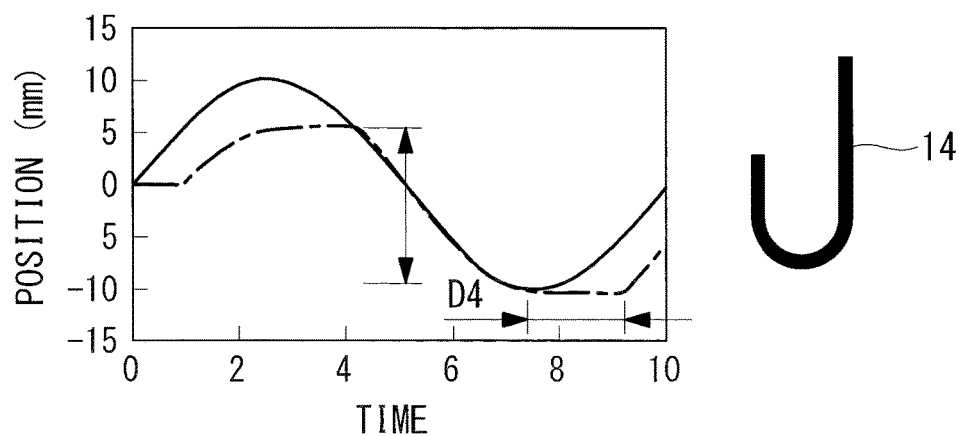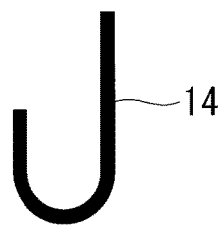

MANIPULATOR SYSTEM

CROSS-REFERENCE TO RELATED APPLICATIONS

This is a continuation of International Application PCT/JP2014/069261, with an international filing date of Jul. 18, 2014, which is hereby incorporated by reference herein in its entirety. This application claims the benefit of Japanese Patent Application No. 2013-154467, filed on Jul. 25, 2013, the content of which is incorporated herein by reference.

TECHNICAL FIELD

The present invention relates to a manipulator system.

BACKGROUND ART

Typical endoscopes or manipulators, composed of an elongated insertion section that is inserted into a subject and an operating unit that is connected to a basal end side of the insertion section, have a bending section at a distal end portion of the insertion section so that the orientation of the distal end can be changed by bending the bending section. Mechanisms for bending the bending section include pulling a basal end portion of a wire connected to the bending section by manually turning a knob provided on the operating unit. Nowadays, the study of technologies for motorizing this bending mechanism is in progress, and technologies for replacing the current manual knob operation with motor driving are being actively studied (e.g., refer to Patent Literatures PTL 1 and PTL 2 below). For typical motor driving, the curvature angle of the bending section can be changed by an amount of curvature corresponding to the amount of operation as a result of the motor being rotated by an amount proportional to the amount of operation applied to the operating unit.

In practice, however, it is difficult to completely transmit the amount of pulling applied to the basal end portion of the wire to the distal end of the wire due to, for example, friction between the wire and members therearound and slackness of the wire. In other words, a nonlinear relationship holds between the amount of wire pulling and the amount of curvature of the bending section. Furthermore, this nonlinearity varies depending on the curved shape of the insertion section. Therefore, it is not possible to achieve superior and constant responsiveness in bending motion of the bending section to an operator's operation merely by making the amount of motor rotation proportional to the amount of operation. It is well known that such a decrease and variation in responsiveness also take place during advancement/retraction motion and rotational motion of a treatment tool disposed in a channel of the insertion section (e.g., see Patent Literature PTL 3 below).

To overcome this, an attempt is made in Patent Literatures PTL 1 through PTL 3 to improve responsiveness by controlling the motor so as to compensate for a decrease or variation in responsiveness in motion of the bending section or the treatment tool on the basis of the curved shape of a flexible section or the bending section. The motion of the treatment tool and the bending section is affected by the curved shapes of both the flexible section and the bending section. In PTL 1 through PTL 3, the curved shape of only one of the flexible section and the bending section is taken into account.

CITATION LIST

Patent Literature

{PTL 1}
Japanese Unexamined Patent Application, Publication No. 2002-264048
{PTL 2}
Publication of Japanese Patent No. 5048158
{PTL 3}
Japanese Unexamined Patent Application, Publication No. 2007-89808

SUMMARY OF INVENTION

A first aspect of the present invention is a manipulator system including: a manipulator that includes an insertion section having an elongated flexible section with flexibility and a bending section provided at a distal end of the flexible section and that includes a bending-section drive unit for causing the bending section to undergo bending motion; an operation input unit via which an operator inputs an operating instruction to the bending section; a flexible-section shape detecting unit that detects a curved shape of the flexible section; a bending-section shape detecting unit that detects a curved shape of the bending section; a control unit that generates a curvature control signal for driving the bending-section drive unit according to the operating instruction input via the operation input unit; and a compensation-value setting unit that sets a compensation value for the curvature control signal on the basis of the curved shape of the flexible section detected by the flexible-section shape detecting unit and the curved shape of the bending section detected by the bending-section shape detecting unit, wherein the control unit corrects the curvature control signal with the compensation value set by the compensation-value setting unit and transmits the corrected curvature control signal to the bending-section drive unit.

A second aspect of the present invention is a manipulator system including: a manipulator having an insertion section that includes an elongated flexible section with flexibility and that includes a bending section provided at a distal end of the flexible section, a treatment tool inserted in the insertion section along a longitudinal direction thereof, and a treatment-tool drive unit that causes the treatment tool to undergo advancement/retraction motion and rotational motion in the insertion section; an operation input unit via which an operator inputs an operating instruction to the treatment tool; a flexible-section shape detecting unit that detects a curved shape of the flexible section; a bending-section shape detecting unit that detects a curved shape of the bending section; a control unit that generates an advancement/retraction control signal and a rotation control signal for driving the treatment-tool drive unit according to the operating instruction input via the operation input unit; and a compensation-value setting unit that sets a compensation value for the advancement/retraction control signal and the rotation control signal on the basis of the curved shape of the flexible section detected by the flexible-section shape detecting unit and the curved shape of the bending section detected by the bending-section shape detecting unit, wherein the control unit corrects the advancement/retraction control signal and the rotation control signal with the compensation values set by the compensation-value setting unit and transmits the advancement/retraction control signal and the rotation control signal to the treatment-tool drive unit.

BRIEF DESCRIPTION OF DRAWINGS

FIG. 6 is an external view of the overall structure of a treatment tool included in the manipulator system in FIG. 1.

FIG. 15A is a graph illustrating a response characteristic of the bending section in normal control when the flexible section is in a straight line.

FIG. 15B is a graph illustrating a response characteristic of the bending section in normal control when the flexible section is curved.

DESCRIPTION OF EMBODIMENTS

First Embodiment

A manipulator system 100 according to a first embodiment of the present invention will now be described with reference to FIGS. 1 through 12.

Figure 1:
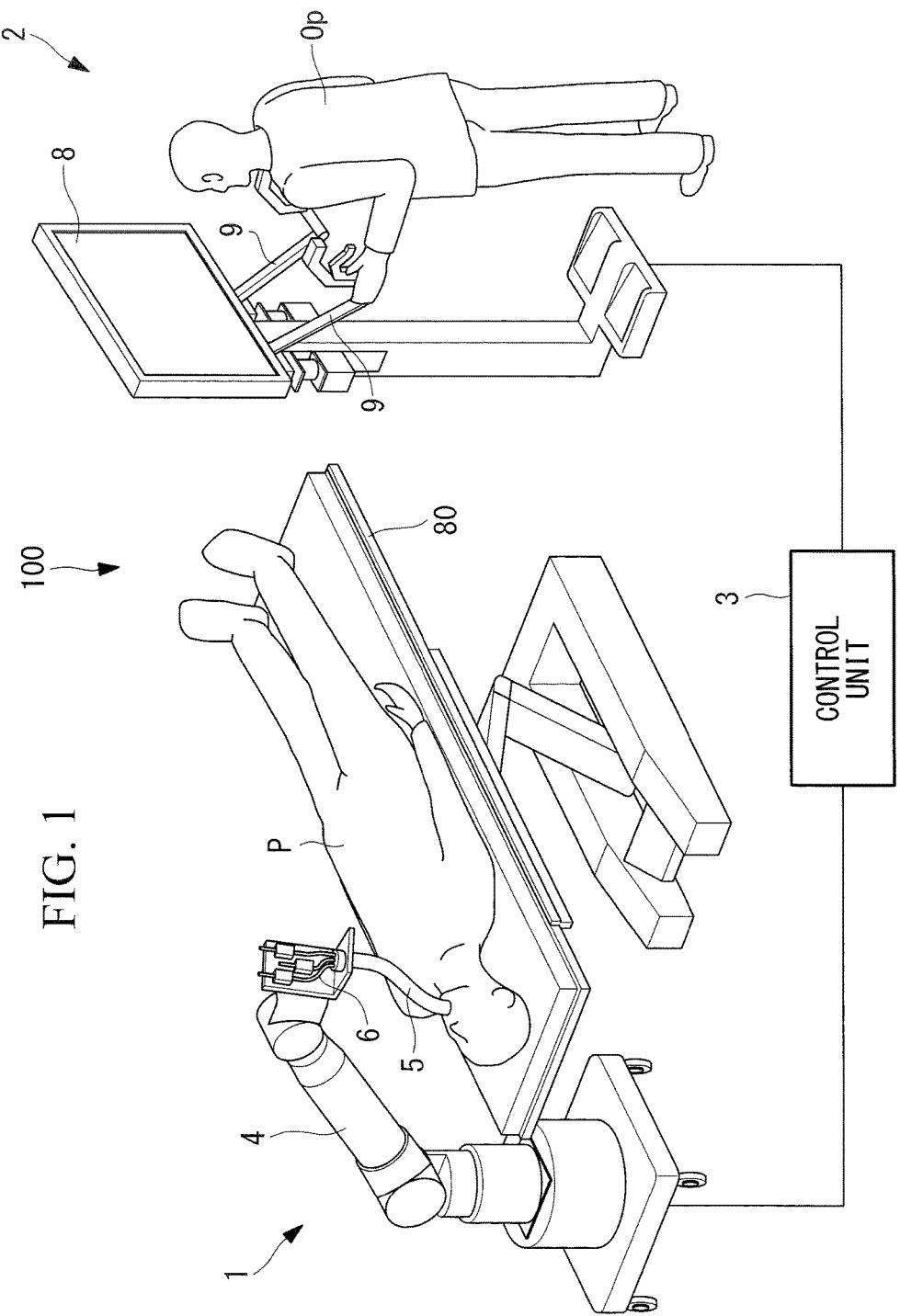
FIG. 1 is an external view of the basic structure of a manipulator system according to a first embodiment of the present invention.

First of all, the outline of the manipulator system 100 of this embodiment will be described. As shown in FIG. 1, the manipulator system 100 of this embodiment includes, as major components, a slave manipulator (manipulator) 1; a master input unit (operation input unit) 2 operated by a practitioner (operator) Op; and a control unit 3 that controls the slave manipulator 1 on the basis of operation applied to the master input unit 2.

Figure 2:
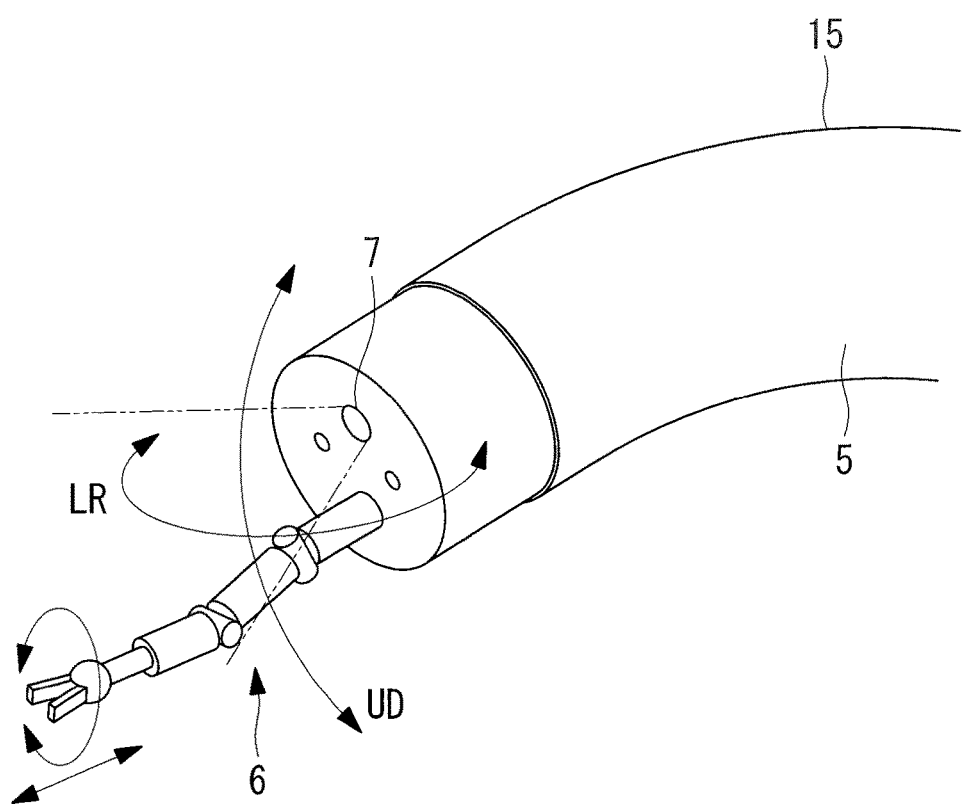
FIG. 2 is an external view of the structure of a distal end portion of an insertion section included in the manipulator system in FIG. 1.

The slave manipulator 1 includes a slave arm 4 disposed adjacent to a surgical table 80 on which a patient P lies; an insertion section 5 retained at a distal end of the slave arm 4; and a treatment tool 6 inserted into the insertion section 5. As shown in FIG. 2, an observation member 7 is provided at a distal end of the insertion section 5 to acquire a video image showing the field of view in front of the distal end of the insertion section 5, as well as the treatment tool 6 protruding from the distal end of the insertion section 5. The video image acquired by the observation member 7 is displayed on a display unit 8 provided at the master input unit 2. The field of view of the observation member 7 is movable by changing the curvature angle of a bending section 15 formed at a distal end portion of the insertion section 5 in the up/down direction (UD direction) or the left/right direction (LR direction) orthogonal to the longitudinal direction of the insertion section 5.

The practitioner Op can remotely operate the insertion section 5 inserted into the body of the patient P and the treatment tool 6 introduced into the body through the insertion section 5 by operating a master arm 9 provided at the master input unit 2 while observing the video image showing the inside of the body and the treatment tool 6 displayed on the display unit 8.

Next, components of the manipulator system 100 will be described in detail.

Figure 3:
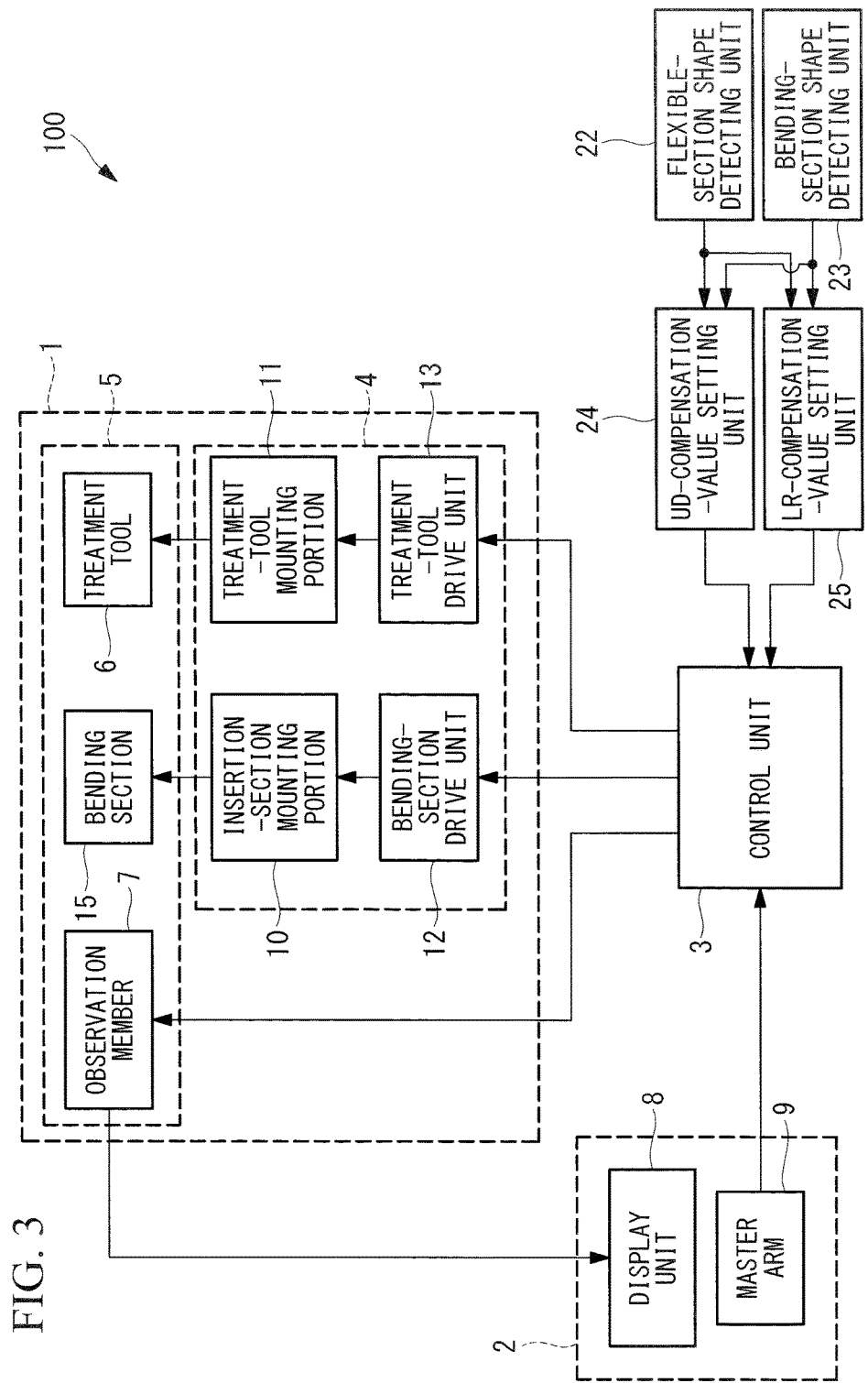
FIG. 3 is a block diagram showing the overall structure of the manipulator system in FIG. 1.

As shown in FIG. 3, the slave arm 4 includes an insertion-section mounting portion 10 at which the insertion section 5 is mounted; a treatment-tool mounting portion 11 at which the treatment tool 6 is mounted; a bending-section drive unit 12 for driving the bending section 15 of the insertion section 5 mounted to the insertion-section mounting portion 10; and a treatment-tool drive unit 13 for driving the treatment tool 6 mounted to the treatment-tool mounting portion 11. The bending-section drive unit 12 and the treatment-tool drive unit 13 drive the bending section 15 and the treatment tool 6, respectively, according to a control signal received from the control unit 3.

Figure 4:
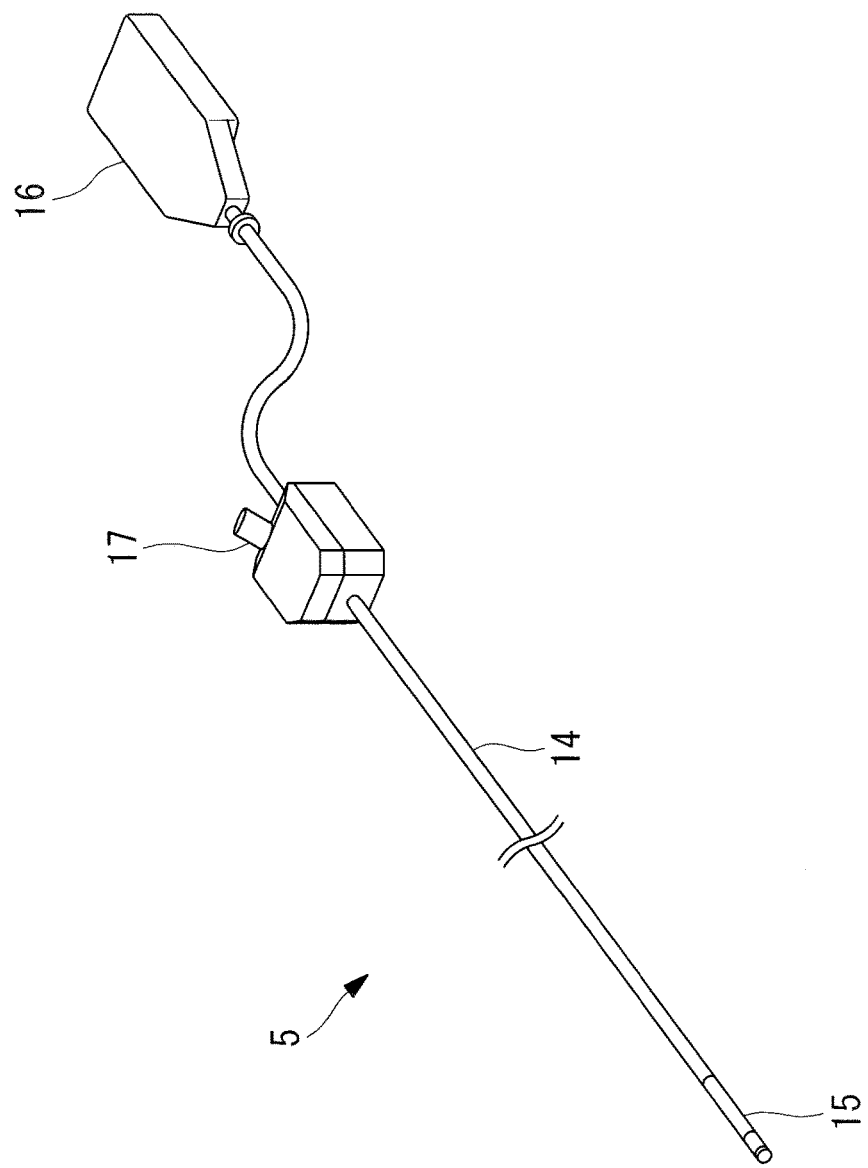
FIG. 4 is an external view of an overall structure of the insertion section included in the manipulator system in FIG. 1.

FIG. 4 shows an external view of the insertion section 5. As shown in FIG. 4, the insertion section 5 includes an elongated flexible section 14 having flexibility; and the bending section 15 provided at a distal end of the flexible section 14. Furthermore, a mounting unit 16 to be mounted to the insertion-section mounting portion 10 of the slave arm 4 is connected to a basal end side of the flexible section 14. The bending section 15 has a known structure of, for example, a plurality of joint rings and bending pieces linked with each other and is constructed so as to bend in the UD direction and the LR direction when the basal end portions of a UD-bending wire 15a (linear member) and an LR-bending wire 15b (linear member) connected to, for example, the joint ring at the most distal end thereof are pushed or pulled in the longitudinal direction in the mounting unit 16.

Figure 5:
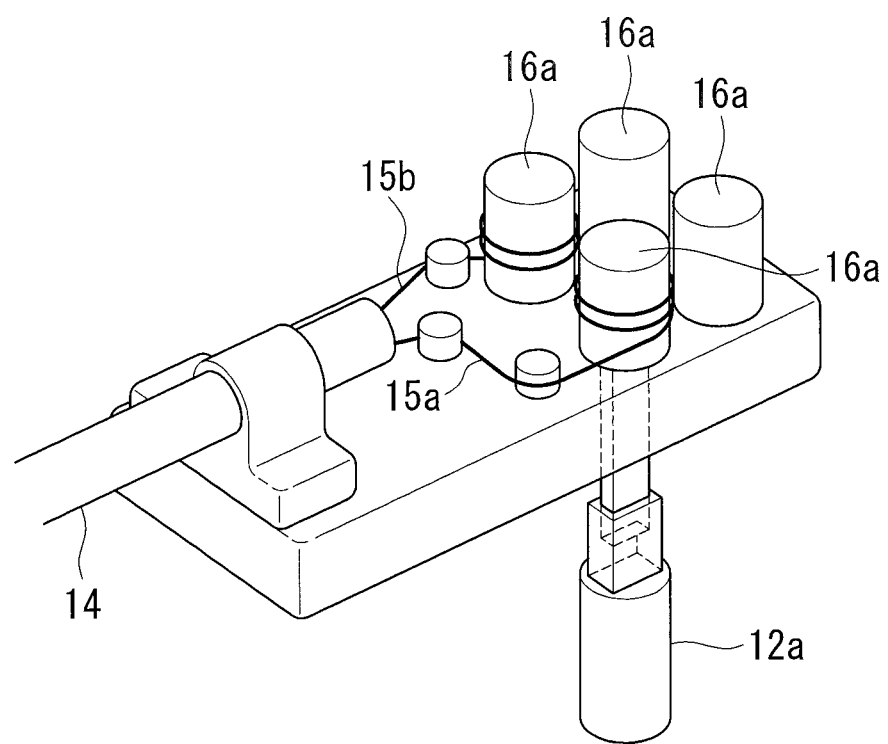
FIG. 5 is a schematic view of a mechanism for bending the bending section in FIG. 4.

More specifically, as shown in FIG. 5, the basal end portion of each of the wires 15a and 15b is pulled out from the basal end of the flexible section 14 and is wound around a pulley 16a provided in the mounting unit 16. The mounting unit 16 is constructed so that when it is mounted to the insertion-section mounting portion 10, each of the pulleys 16a is coaxially linked to a motor 12a of the bending-section drive unit 12. When the motor 12a is rotated according to a rotation control signal from the control unit 3, the pulley 16a rotates in the normal or reverse direction, which causes the wire 15a or 15b to be pushed and pulled to change the curvature angle of the bending section 15. FIG. 5 illustrates only one motor 12a and only two wires 15a and 15b wound around two pulleys 16a on the flexible section 14 side for the sake of simplicity of the drawing.

In addition, the insertion section 5 includes a channel formed so as to penetrate therethrough in the longitudinal direction thereof. This channel communicates with a treatment-tool port 17 provided at the basal end side of the insertion section 5 so that the treatment tool 6 is inserted via the treatment-tool port 17 into the channel.

The treatment tool 6 is an instrument such as a high-frequency knife, a snare loop, or grasping forceps and, as shown in FIG. 6, includes an elongated main body 18 having flexibility and a treatment part 19 provided at the distal end of the main body 18. In addition, a mounting unit 20 to be mounted to the treatment-tool mounting portion 11 of the slave arm 4 is connected to the basal end side of the main body 18. When the basal end portion of the main body 18 is pushed and pulled in the longitudinal direction or rotated in the circumferential direction in the mounting unit 20, the entire treatment tool 6 is advanced/retracted or rotated in the channel.

More specifically, a pulley 20a coaxially linked to the basal end of the main body 18 is provided in the mounting unit 20. This pulley 20a is fixed to a stage 20b that can move linearly in the longitudinal direction of the main body 18. Meanwhile, the treatment-tool drive unit 13 is provided with a rotation motor 13a for rotating the pulley 20a and a linear motor 13b for linearly moving the stage 20b. The mounting unit 20 is structured so as to link the pulley 20a with the rotation motor 13a and link the stage 20b with the linear motor 13b when it is mounted to the treatment-tool mounting portion 11. Because of this, when the rotation motor 13a rotates the pulley 20a according to the rotation control signal from the control unit 3, the treatment tool 6 rotates. Furthermore, the treatment tool 6 is advanced/retracted by the linear motor 13b linearly moving the stage 20b according to an advancement/retraction control signal from the control unit 3.

As described above, the master input unit 2 includes the display unit 8 for displaying a video image acquired by the observation member 7 and a plurality of the master arms 9 operated by the practitioner Op. Each of the master arms 9 is configured to allow the practitioner Op to enter an operating instruction for at least the bending section 15 and the treatment tool 6. The master input unit 2 generates an operating signal according to the operating instruction input to the master arm 9 by the practitioner Op and transmits the generated operating signal to the control unit 3.

Upon receiving the operating signal for the bending section 15 from the master input unit 2, the control unit 3 generates a curvature control signal for driving the bending-section drive unit 12 on the basis of the operating signal and transmits the curvature control signal to the bending-section drive unit 12. Furthermore, upon receiving the operating signal for the treatment tool 6 from the master input unit 2, the control unit 3 generates, on the basis of the operating signal, the advancement/retraction control signal and the rotation control signal for driving the treatment-tool drive unit 13 and transmits the advancement/retraction control signal and rotation control signal to the treatment-tool drive unit 13. The motors 12a, 13a, and 13b of the drive units 12 and 13 are provided with an encoder (not shown in the figure) for detecting the amount of rotation thereof. The control unit 3 receives the amount of rotation of each of the motors 12a, 13a, and 13b from the encoders to recognize the amount of curvature of the bending section 15 and the amounts of advancement/retraction and rotation of the treatment tool 6 and feedback (FB) controls the motor of each of the drive units 12 and 13 on the basis of these recognized amounts.

The manipulator system 100 of this embodiment further includes a flexible-section shape detecting unit 22 for detecting a curved shape of the flexible section 14; a bending-section shape detecting unit 23 for detecting a curved shape of the bending section 15; and compensation-value setting units 24 and 25. The compensation-value setting units 24 and 25 set compensation values according to the curved shapes of the flexible section 14 and the bending section 15 detected by the shape detecting units 22 and 23, respectively. The control unit 3 feedforward (FF) controls the bending-section drive unit 12 using the compensation values set by the compensation-value setting units 24 and 25 so that the bending motion of the bending section 15 accurately follows the operating signal. A method for controlling the bending section 15 with this control unit 3 will be described in detail.

The flexible-section shape detecting unit 22 includes an endoscope-insertion-shape monitoring device for acquiring the shape of the flexible section 14 by detecting magnetism produced by a magnetic coil incorporated in the flexible section 14. The flexible-section shape detecting unit 22 calculates a feature quantity k representing the curved shape of the flexible section 14 on the basis of the shape of the flexible section 14 acquired by the endoscope-insertion-shape monitoring device.

A plurality of the magnetic coils are provided at different positions along the longitudinal direction of the flexible section 14. The endoscope-insertion-shape monitoring device includes an antenna for receiving magnetism produced by each of the magnetic coils, and the position of each of the magnetic coils is calculated from the magnetism received by the antenna, thus acquiring the curved shape of the flexible section 14 by connecting the obtained positions of the magnetic coils with a smooth curve.

Figure 7A:
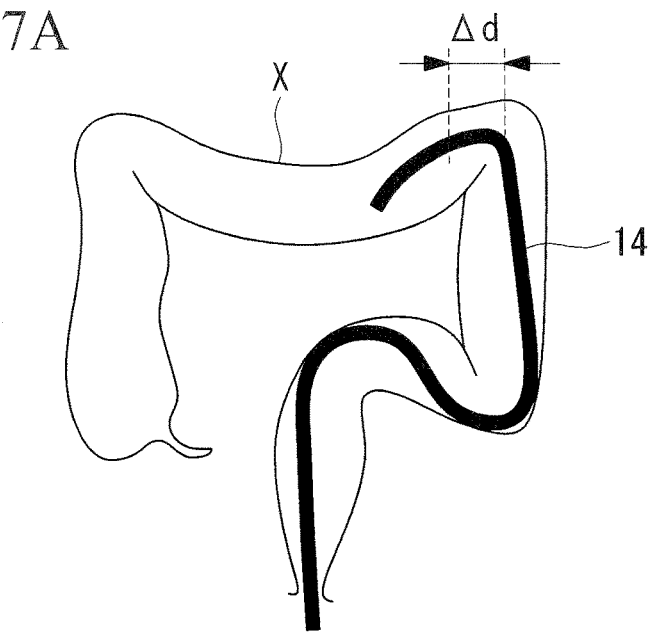
FIG. 7A is a diagram illustrating a method for calculating a feature quantity k with a flexible-section shape detecting unit in FIG. 4, showing a curved shape of the flexible section detected by the flexible-section shape detecting unit.
Figure 7B:
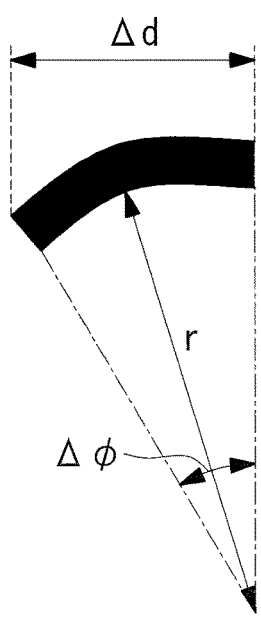
FIG. 7B is a diagram illustrating a method for calculating a feature quantity k with the flexible-section shape detecting unit in FIG. 4, showing variables regarding an infinitesimal.

On the basis of the curved shape of the flexible section 14 acquired by the endoscope-insertion-shape monitoring device, the flexible-section shape detecting unit 22 calculates the feature quantity k by following the procedure below. First, as shown in FIGS. 7A and 7B, the flexible-section shape detecting unit 22 divides the flexible section 14 into infinitesimals Δd in the longitudinal direction, and a radius of curvature r and a curvature angle Δφ of each of the infinitesimals Δd are measured. The flexible-section shape detecting unit 22 stores a function for defining the relationship between a feature quantity Δk and the radius of curvature r and the curvature angle Δφ of an infinitesimal Δd. This function is set so that the feature quantity Δk is zero when the flexible section 14 extends in a straight line (i.e., when r=∞ and the curvature angle Δφ=0) and that the smaller the radius of curvature r and the larger the curvature angle Δφ become, the larger the feature quantity Δk becomes. By substituting the radius of curvature r and the curvature angle Δφ into this function, the feature quantity Δk for each of the infinitesimals Δd can be obtained. Thereafter, by integrating the feature quantities Δk spanning the total length of the flexible section 14, the feature quantity k representing the amount of curvature of the curved shape of the entire flexible section 14 is calculated. Reference sign X in FIG. 7A represents a colon through which the insertion section 5 is inserted.

The feature quantity k may also be calculated using either one of the radius of curvature r and the curvature angle Δφ.

Also, the flexible-section shape detecting unit 22 may detect the curved shape of the flexible section 14 using another means instead of the endoscope-insertion-shape monitoring device. For example, the flexible-section shape detecting unit 22 may detect an actual curvature angle of the flexible section 14 with a bend sensor provided at a plurality of positions in the longitudinal direction of the flexible section 14. As the bend sensor, for example, a strain sensor or an optical fiber sensor is employed.

Figure 8A:
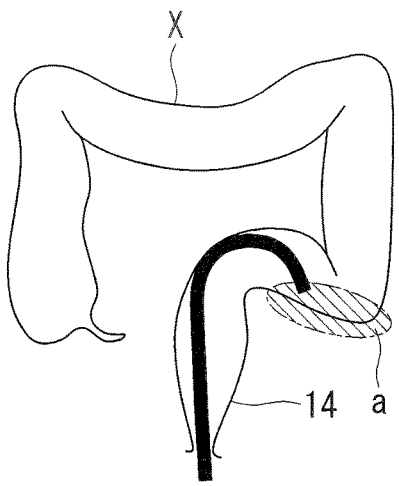
FIG. 8A is a diagram illustrating another method for calculating a feature quantity k with the flexible-section shape detecting unit in FIG. 4.
Figure 8B:
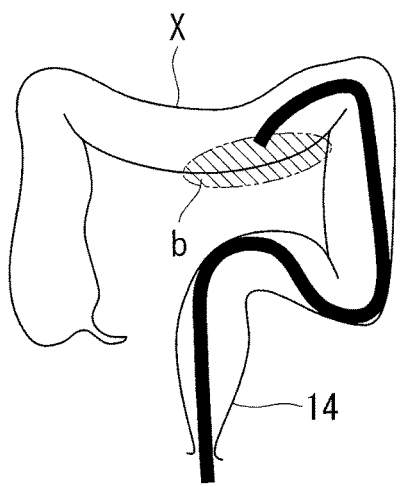
FIG. 8B is a diagram illustrating another method for calculating the feature quantity k with the flexible-section shape detecting unit in FIG. 4.
Figure 8C:
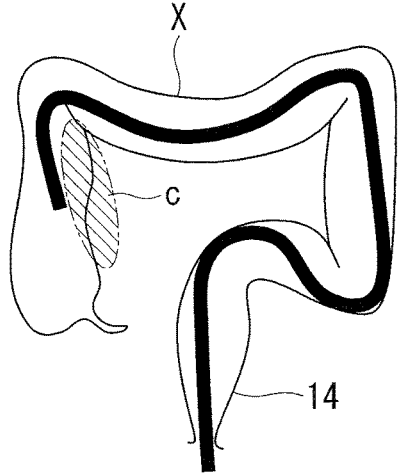
FIG. 8C is a diagram illustrating another method for calculating the feature quantity k with the flexible-section shape detecting unit in FIG. 4.

Alternatively, the flexible-section shape detecting unit 22 may detect the curved shape of the flexible section 14 on the basis of the shape of an intracorporeal region in which the flexible section 14 is disposed. For example, when the flexible section 14 is inserted into the colon X, the shape of the flexible section 14 in the body is substantially identical to the shape of the colon X. Therefore, the shape of the region in the body into which the flexible section 14 is inserted can be adopted as the curved shape of the flexible section 14. In this case, because the curved shape of the entire flexible section 14 differs depending on the position of the inserted flexible section 14, it is preferable that the above-described feature quantity k be stored for each of the curved shapes of the flexible section 14 corresponding to, for example, a plurality of regions a, b, and c to be treated, as shown in FIGS. 8A through 8C.

The bending-section shape detecting unit 23 detects the curvature angles $\theta_{UD}$ and $\theta_{LR}$ in the UD direction and the LR direction of the bending section 15 on the basis of the curvature control signal transmitted by the control unit 3 to the bending-section drive unit 12. Subsequently, the bending-section shape detecting unit 23 transmits the curvature angle $\theta_{LR}$ in the LR direction to the UD-compensation-value setting unit 24 and transmits the curvature angle $\theta_{UD}$ in the UD direction to the LR-compensation-value setting unit 25.

Instead of on the basis of the curvature control signal, the bending-section shape detecting unit 23 may detect the curved shape of the bending section 15 on the basis of an output from an encoder provided in the motor 12a of the bending-section drive unit 12. Alternatively, the bending-section shape detecting unit 23 may use, for example, the above-described endoscope-insertion-shape monitoring device or the bend sensor.

The compensation-value setting units include a UD-compensation-value setting unit (compensation-value setting unit) 24 for setting the compensation value for the UD direction and an LR-compensation-value setting unit (compensation-value setting unit) 25 for setting the compensation value for the LR direction.

The UD-compensation-value setting unit 24 calculates an FF gain $Gff_{UD}$ for feedforward (FF) control of bending motion in the UD direction of the bending section 15 by the control unit 3, from expression (1) below, using the feature quantity k calculated by the flexible-section shape detecting unit 22 and the curvature angle $\theta_{LR}$ detected by the bending-section shape detecting unit 23.

$$Gff_{UD}=gff_{UD}\times\alpha_{UD}(\theta_{LR})\times\beta_{ff}(k) \tag{1}$$

Here, $gff_{UD}$ is an FF gain when the flexible section 14 and the bending section 15 extend in a straight line (i.e., when $\theta_{LR}=k=0$), $\alpha_{UD}(\theta_{LR})$ is a compensation factor according to the curvature angle $\theta_{LR}$, and $\beta_{ff}(k)$ is a compensation factor according to the feature quantity k. However, $\alpha_{UD}(0)=1$ and $\beta_{ff}(0)=1$.

The compensation factor $\alpha_{UD}(\theta_{LR})$ is a proportional function or a polynomial function of the curvature angle $\theta_{LR}$ and differs depending on dynamic characteristics of the bending section 15. The compensation factor $\alpha_{UD}(\theta_{LR})$ is experimentally determined, for example, by measuring, with various curvature angles $\theta_{LR}$ in the LR direction, the relationship between the curvature control signal input to the bending-section drive unit 12 and the actual curvature angle $\theta_{UD}$ of the bending section 15 in the UD direction. Alternatively, the compensation factor $\alpha_{UD}(\theta_{LR})$ may be theoretically determined by simulation based on mechanical characteristics or dynamic characteristics. A mechanical characteristic represents a characteristic such as a dimension or a shape on the basis of, for example, mechanical design drawings. Or alternatively, the compensation factor $\alpha_{UD}(\theta_{LR})$ may be determined by combining a theoretical approach and an experimental approach.

The compensation factor $\beta_{ff}(k)$ is a proportional function or a polynomial function of the feature quantity k and differs depending on a dynamic characteristic of the flexible section 14. The compensation factor $\beta_{ff}(k)$ is experimentally determined, for example, by measuring, with various curved shapes of the flexible section 14, the relationship between the curvature control signal input to the bending-section drive unit 12 and an actual curvature angle $\theta_{UD}$ of the bending section 15 in the UD direction. Alternatively, the compensation factor $\beta_{ff}(k)$ may be theoretically determined by simulation based on a mechanical characteristic or a dynamic characteristic. Or alternatively, the compensation factor $\beta_{ff}(k)$ may be determined by combining a theoretical approach and an experimental approach.

Likewise, the LR-compensation-value setting unit 25 calculates an FF gain $Gff_{LR}$ for FF control of bending motion in the LR direction of the bending section 15 by the control unit 3, from expression (2) below, using the curvature angle $\theta_{UD}$ and the feature quantity k.

$$Gff_{LR}=gff_{LR}\times\alpha_{LR}(\theta_{UD})\times\beta_{ff}(k) \tag{2}$$

where $gff_{LR}$ is an FF gain when the flexible section 14 and the bending section 15 extend in a straight line (i.e., when $\theta_{UD}$=k=0), and $\alpha_{LR}(\theta_{UD})$ is a compensation factor according to the curvature angle $\theta_{UD}$ of the bending section 15. However, $\alpha_{LR}(0)$=1.

The control unit 3 amplifies the curvature control signal by multiplying the curvature control signal generated from the operating signal input from the master input unit 2 by the FF gains $Gff_{UD}$ and $Gff_{LR}$ obtained from expression (1) and expression (2) and transmits the amplified curvature control signal to the bending-section drive unit 12. By doing so, the bending-section drive unit 12 is FF-controlled.

Next, the operation of the manipulator system 100 with the aforementioned structure will be described.

As shown in FIG. 1, in order to treat the inside of the body using the manipulator system 100 of this embodiment, the practitioner Op first inserts the insertion section 5 into the body via a natural opening (the mouth in the illustrated example) of the patient P. While observing on the display unit 8 the video image acquired by the observation member 7, the practitioner Op moves the distal end of the insertion section 5 to the intended region.

Then, the practitioner Op pushes the treatment tool 6 disposed in the channel of the insertion section 5 out from the opening at the distal end of the insertion section 5. Thereafter, the practitioner Op adjusts the positional relationship between the treatment part 19 and the intended region in the body by changing the curvature angle of the bending section 15 or the amount of protrusion and the rotational direction of the treatment tool 6 while observing the video image displayed on the display unit 8 and administers treatment to the intended region with the treatment part 19.

At this time, when the practitioner Op inputs, to the master arm 9, an operation for changing the curvature angle of the bending section 15, an operating signal according to this operation is transmitted from the master arm 9 to the control unit 3. The control unit 3 generates a curvature control signal for bending the bending section 15 in the LR direction or in the UD direction according to the received operating signal. Meanwhile, the compensation-value setting units 24 and 25 set the FF gains $Gff_{UD}$ and $Gff_{LR}$ on the basis of the curved shapes of the flexible section 14 and the bending section 15 at that time and transmit the FF gains $Gff_{UD}$ and $Gff_{LR}$ to the control unit 3. The control unit 3 FF-controls the bending-section drive unit 12 by transmitting to the bending-section drive unit 12 the curvature control signal amplified with the FF gains $Gff_{UD}$ and $Gff_{LR}$.

The responsiveness in bending motion of the bending section 15 to the operation input by the practitioner Op to the master arm 9 will be described below.

Figure 9A:
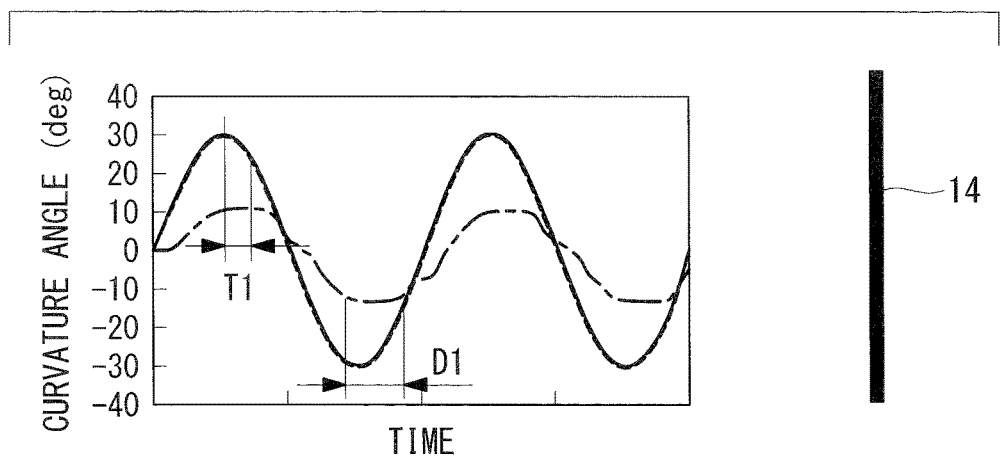
FIG. 9A is a graph depicting a response characteristic of the bending section in normal control when the flexible section is in a straight line.
Figure 9B:
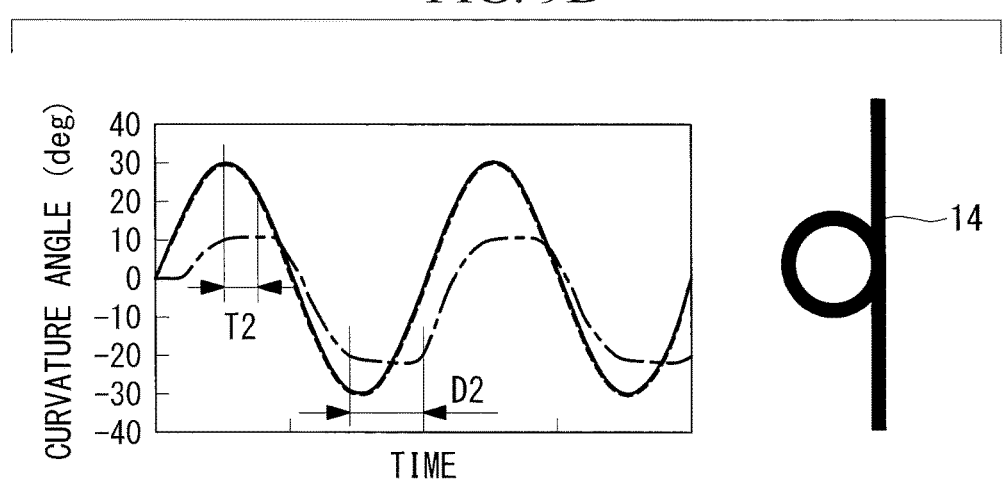
FIG. 9B is a graph depicting a response characteristic of the bending section in normal control when the flexible section is curved.
Figure 9C:
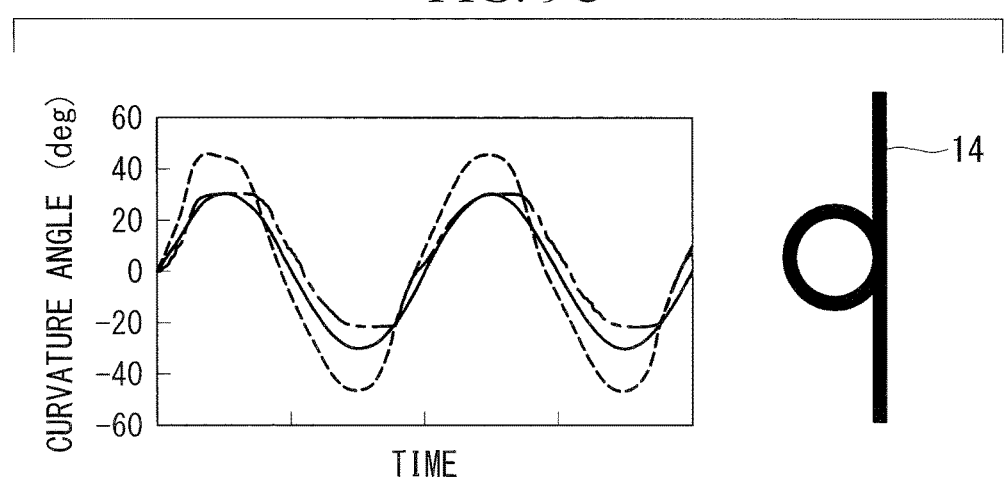
FIG. 9C is a graph depicting a response characteristic of the bending section in FF control when the flexible section is curved.

FIGS. 9A through 9C illustrate response characteristics of the bending section 15 to the operating signal. FIG. 9A is a graph for the case where the flexible section 14 extends in a straight line, whereas FIGS. 9B and 9C are graphs for the case where the flexible section 14 is bent by 360° so as to form a circle with a diameter of 150 mm. In FIGS. 9A through 9C, the solid lines represent the curvature angle specified by the operating signal input to the control unit 3, the broken lines represent the curvature angle of the bending section 15 theoretically calculated from an output of the encoder provided in the bending-section drive unit 12, and the chain lines represent an actual curvature angle of the bending section 15.

As shown in FIGS. 9A and 9B, in normal control (i.e., without FF control) in which the motor 12a is controlled so that the amount of rotation of the motor 12a is proportional to the amount of operation input to the master arm 9, delay times T1 and T2 occur from when the motor 12a starts rotating to when the bending section 15 moves. Furthermore, there occur deadbands D1 and D2 in which bending motion of the bending section 15 does not respond to the rotation of the motor 12a. It is understood that the delay times T1 and T2 and the deadbands D1 and D2 are larger when the flexible section 14 is curved than when the flexible section 14 is in a straight line. These differences in delay times T1 and T2 and the deadbands D1 and D2 indicate that responsiveness in bending motion of the bending section 15 to operation input by the practitioner Op to the master arm 9 differs depending on the shape of the flexible section 14.

Such a decrease and variation in responsiveness in bending motion of the bending section 15 occurs for the following reason. The force of the motor 12a pulling the basal end portions of the wires 15a and 15b weakens until it reaches the distal ends of the wires 15a and 15b because of factors such as friction between the wires 15a and 15b in bending the bending section 15 and members therearound or slackness of the wires 15a and 15b. Because of this, the actual amount of curvature of the bending section 15 in reaction to the amount of rotation of the motor 12a decreases. The above-described friction or slackness differs depending on the curved shape of the flexible section 14, and it is likely that the larger the amount of curvature of the entire flexible section 14, the larger the friction and slackness. As a result, even if the practitioner Op inputs the same operation to the master arm 9, a variation in responsiveness in bending motion of the bending section 15 occurs depending on the curved shape of the flexible section 14. For the same reason, a variation in responsiveness of the bending section 15 also occurs depending on a difference in the curvature angles $\theta_{UD}$ and $\theta_{LR}$ of the bending section 15.

FIG. 9C illustrates a response characteristic of the bending section 15 when the bending-section drive unit 12 is FF-controlled in a state where the flexible section 14 is bent 360° as in FIG. 9B. As is understood from FIG. 9C, the delay times T1 and T2 and the deadbands D1 and D2 noticeable in FIGS. 9A and 9B are dramatically eliminated, indicating that the responsiveness of the bending section 15 to the operating signal is enhanced. Although not shown in the figure, superior responsiveness, as in FIG. 9C, is also achieved when the flexible section 14 is in a straight line. In this manner, high response sensitivity of the bending section 15 that is achieved regardless of the shape of the flexible section 14 means that no matter what a curved shape the flexible section 14 takes, superior and constant responsiveness of the bending section 15 can always be achieved in response to the operation input by the practitioner Op to the master arm 9.

Thus, according to this embodiment, a decrease or variation in responsiveness of the bending section 15 can be compensated for with high accuracy by amplifying the curvature control signal for bending the bending section 15 on the basis of the curved shapes of both the flexible section 14 and the bending section 15. Because of this, an advantage is afforded in that a superior and constant responsiveness in bending motion of the bending section 15 can be achieved at all times. In particular, bending motion in the UD direction and bending motion in the LR direction of the bending section 15 affect each other. Therefore, a decrease or variation in responsiveness in bending motion in the UD and LR directions can be compensated for with high accuracy by reflecting the curvature angle $\theta_{LR}$ in the LR direction on curvature control in the UD direction and reflecting the curvature angle $\theta_{UD}$ in the UD direction on curvature control in the LR direction.

Although, in this embodiment, the compensation-value setting units 24 and 25 set the FF gains $Gff_{UD}$ and $Gff_{LR}$ as the compensation values, other compensations value can be set.

For example, the compensation-value setting units 24 and 25 may set an FB gain used for FB control of the bending-section drive unit 12 by the control unit 3.

As described above, the control unit 3 FB-controls the motor 12a on the basis of the amount of rotation of the motor 12a detected by the encoder. For this reason, on the basis of the curved shapes of the flexible section 14 and the bending section 15, the compensation-value setting units 24 and 25 may set an FB gain used for FB control. Also in this manner, a decrease or variation in responsiveness of the bending section 15, dependent on a difference in the curved shapes of the flexible section 14 and the bending section 15, can be compensated for with high accuracy.

Figure 10:
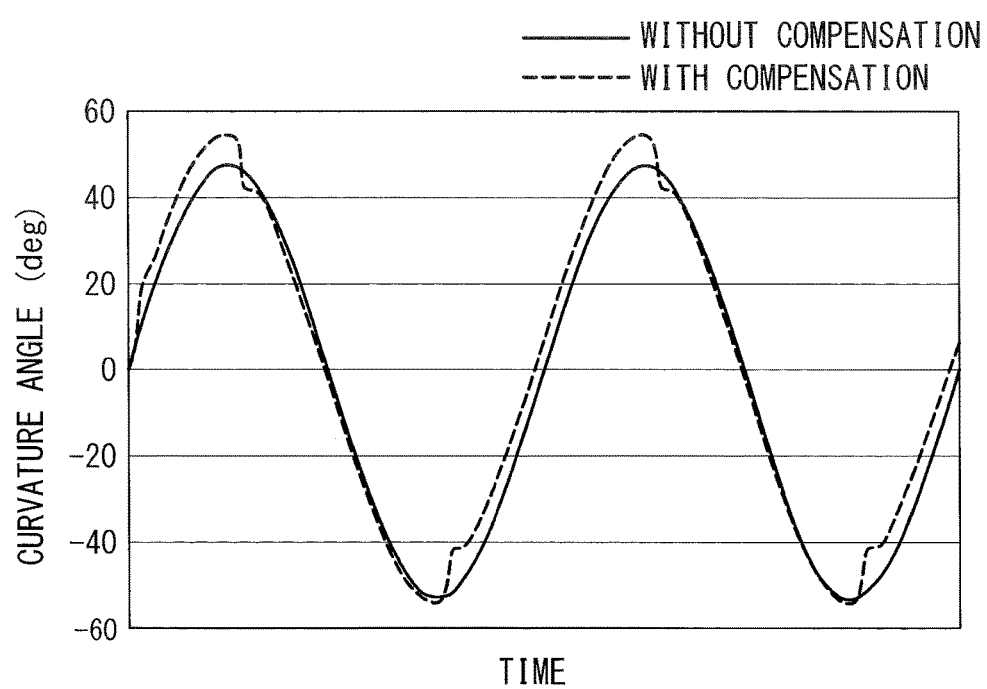
FIG. 10 is a diagram illustrating another method for controlling a bending-section drive unit with a control unit, in the form of a graph depicting control signals before (solid lines) and after (broken line) being corrected with a friction compensation factor.

Alternatively, the compensation-value setting units 24 and 25 may set a friction compensation factor (offset signal) to be superimposed by the control unit 3 on the curvature control signal. As shown in FIG. 10, the friction compensation factor is set so that the amount of offset of the curvature control signal is larger at a turning point where the bending motion of the bending section 15 switches to the reverse direction. By doing so, especially a backlash produced when bending motion is switched in the reverse direction (e.g., when the bending is switched from the L direction to the R direction) can be reduced, allowing the above-described deadbands D1 and D2 to be eliminated effectively.

Figure 11:
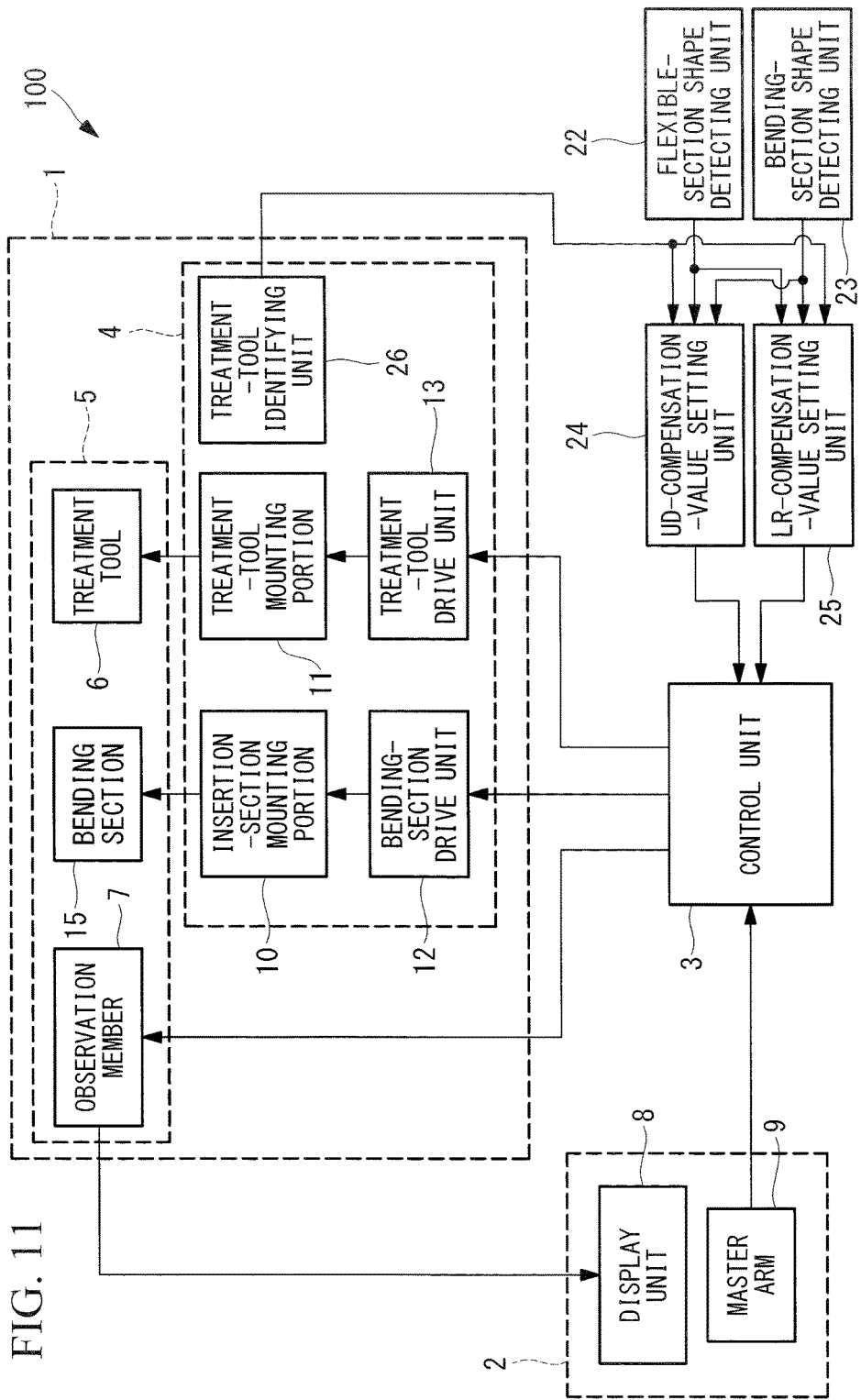
FIG. 11 is a block diagram showing a modification of the manipulator system in FIG. 1.

As shown in FIG. 11, this embodiment may further include a treatment-tool identifying unit 26 that determines whether the treatment tool 6 is present in the channel and that, if the treatment tool 6 is present in the channel, identifies the treatment tool 6, so that the compensation-value setting units 24 and 25 may set a compensation value by taking into account the presence or absence of the treatment tool 6 and, if the treatment tool 6 is present in the channel, the dynamic characteristics of the treatment tool 6, in addition to the curved shapes of the flexible section 14 and the bending section 15.

The mounting unit 20 of the treatment tool 6 is provided with a recording medium, such as a barcode or an integrated circuit tag, storing identification information for identifying the treatment tool 6.

The treatment-tool identifying unit 26 reads out the identification information recorded on the recording medium of the mounting unit 20 provided at the treatment-tool mounting portion 11 and transmits the read-out identification information to the compensation-value setting units 24 and 25.

The treatment-tool identifying unit 26 may be constructed so as to identify the treatment tool 6 electrically or magnetically. For example, the mounting unit 20 may be provided with a magnet or resistor having characteristics that differ depending on the treatment tool 6, so that the treatment-tool identifying unit 26 can detect the characteristics of the magnet or the resistor. Alternatively, the treatment-tool identifying unit 26 may be realized by an input device such as a keyboard, a touch panel, or a button.

The compensation-value setting units 24 and 25 store a combination of the compensation factors $\alpha_{UD}(\theta_{LR})$, $\alpha_{LR}(\theta_{UD})$ and $\beta_{ff}(k)$ having dynamic characteristics that differ for each item of identification information of the treatment tool 6. The compensation-value setting units 24 and 25 select the combination of the compensation factors $\alpha_{UD}(\theta_{LR})$, $\alpha_{LR}(\theta_{UD})$, and $\beta_{ff}(k)$ corresponding to the identification information received from the treatment-tool identifying unit 26 and calculate FF gains $Gff_{UD}$ and $Gff_{LR}$ using the selected compensation factors $\alpha_{UD}(\theta_{LR})$, $\alpha_{LR}(\theta_{UD})$ and (k).

The responsiveness of the bending section 15 differs depending on whether or not the treatment tool 6 is present in the channel and, if the treatment tool 6 is present in the channel, the dynamic characteristics (e.g., stiffness and friction factor) of the treatment tool 6, as well. For example, the responsiveness of the bending section 15 is lower when the treatment tool 6 is present in the channel than when the treatment tool 6 is not present in the channel. For this reason, a variation in the responsiveness of the bending section 15 can be compensated for with still higher accuracy by taking into account the presence/absence and the dynamic characteristics of the treatment tool 6.

Figure 12A:
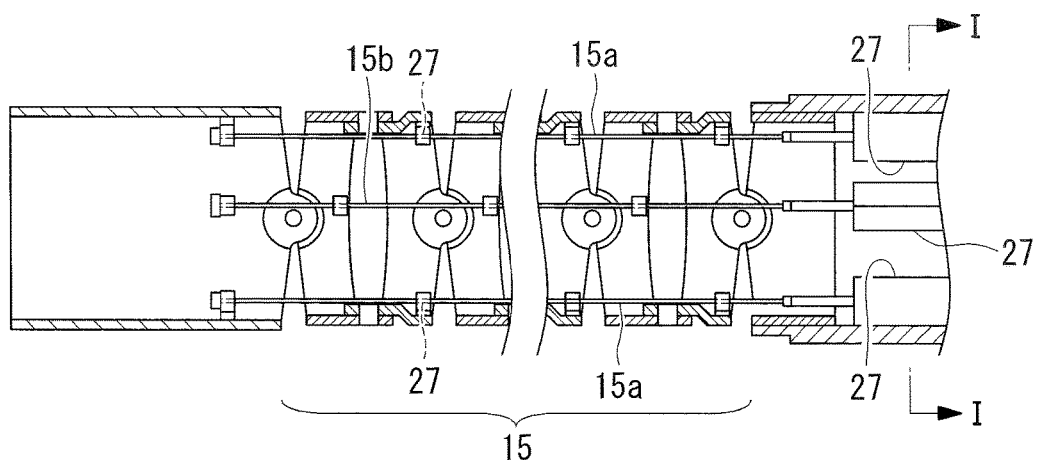
FIG. 12A is a partial longitudinal sectional view of a modification of the insertion section.
Figure 12B:
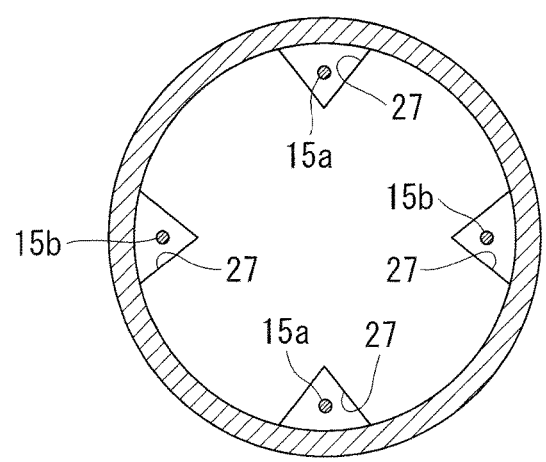
FIG. 12B is a cross-sectional view taken along line I-I in FIG. 12A.

Furthermore, in this embodiment, paths 27 for determining the positions of the wires 15a and 15b for bending the bending section 15 may be formed in the flexible section 14 and the bending section 15, as shown in FIGS. 12A and 12B. In the bending section 15, these paths 27 are realized by a ring-shaped member fixed on an inner circumferential surface of the joint ring. In the flexible section 14, the paths 27 are formed so as to penetrate through the flexible section 14 along the longitudinal direction thereof, forming a space separated from spaces in which members other than the wires 15a and 15b are disposed.

In a case where the wires 15a and 15b are freely movable in the radial direction in the flexible section 14 and the bending section 15, the optimal compensation value may differ between the flexible section 14 and the bending section 15 even if the flexible section 14 and the bending section 15 take an identical curved shape. This is because friction or slackness produced in the wires 15a and 15b may differ between the wires 15a and 15b due to a variation occurring in the routes of the wires 15a and 15b. Therefore, a decrease or variation in responsiveness in bending motion of the bending section 15 can be compensated for with still higher accuracy by causing the paths 27 to determine the routes of the wires 15a and 15b in the flexible section 14 and the bending section 15 and also preventing the wires 15a and 15b from coming into irregular contact with another member.

Second Embodiment

A manipulator system 200 according to a second embodiment of the present invention will now be described with reference to FIG. 13.

In this embodiment, differences from the above-described first embodiment will mainly be described, and structures in common with those in the first embodiment will be denoted with the same reference signs and descriptions thereof will be omitted.

Figure 13:
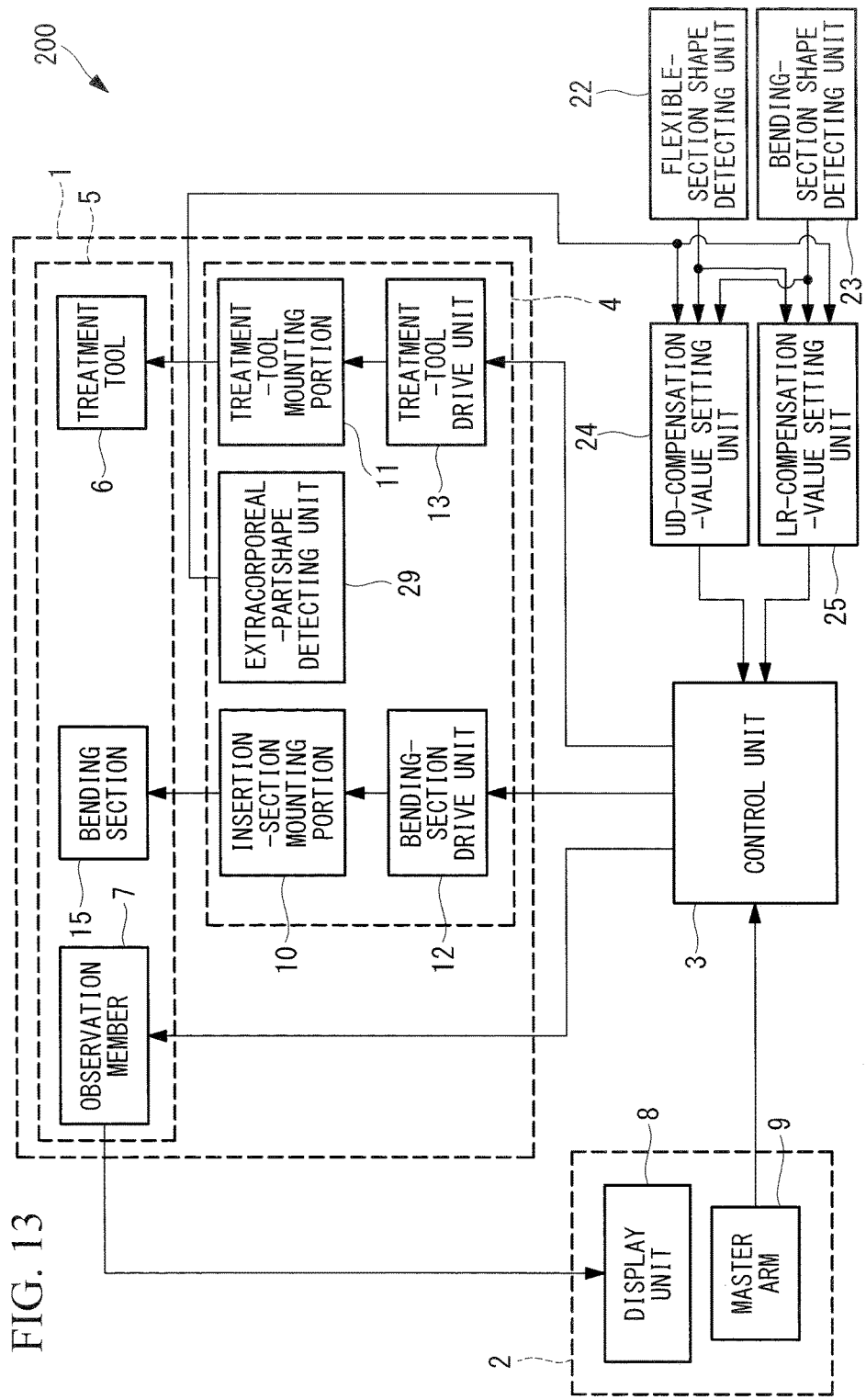
FIG. 13 is a block diagram showing the overall structure of a manipulator system according to a second embodiment of the present invention.

As shown in FIG. 13, the manipulator system 200 of this embodiment differs from the first embodiment mainly in that an extracorporeal-part shape detecting unit 29 for identifying the mounting unit 16 of the insertion section 5 is further included.

The mounting unit 16 is provided with a recording medium that stores identification information for identifying the mounting unit 16.

The extracorporeal-part shape detecting unit 29 reads out the identification information recorded on the recording medium of the mounting unit 16 mounted to the insertion-section mounting portion 10 and transmits the read-out identification information to the compensation-value setting units 24 and 25.

The recording medium and other structures of the extracorporeal-part shape detecting unit 29 are the same as the recording medium and those of the treatment-tool identifying unit 26 provided in the mounting unit 20 described in the first embodiment.

For the mounting unit 16, the UD-compensation-value setting unit 24 stores a combination of the compensation factors $\alpha_{UD}(\theta_{LR})$ and $\beta_{ff}(k)$ having dynamic characteristics that differ for each item of identification information. The UD-compensation-value setting unit 24 selects the combination of the compensation factors $\alpha_{UD}(\theta_{LR})$ and $\beta_{ff}(k)$ corresponding to the identification information for the mounting unit 16 received from the extracorporeal-part shape detecting unit 29 and calculates an FF gain $Gff_{UD}$ from expression (1) using the selected compensation factors $\alpha_{UD}(\theta_{LR})$ and $\beta_{ff}(k)$. In this embodiment, the compensation factors $\alpha_{UD}(\theta_{LR})$ and $\beta_{ff}(k)$ are set according to the routing shape of the UD-bending wire 15a in each of the mounting units 16.

For the mounting unit 16, the LR-compensation-value setting unit 25 stores a combination of the compensation factors $\alpha_{LR}(\theta_{UD})$ and $\beta_{ff}(k)$ having dynamic characteristics that differ for each item of identification information. The LR-compensation-value setting unit 25 selects the combination of the compensation factors $\alpha_{LR}(\theta_{UD})$ and $\beta_{ff}(k)$ corresponding to the identification information received from the extracorporeal-part shape detecting unit 29 and calculates an FF gain $Gff_{LR}$ from expression (2) using the selected compensation factors $\alpha_{LR}(\theta_{UD})$ and $\beta_{ff}(k)$. In this embodiment, the compensation factors $\alpha_{LR}(\theta_{UD})$ and $\beta_{ff}(k)$ are set according to the routing shape of the LR-bending wire 15b in each of the mounting units 16.

According to the manipulator system 200 of this embodiment, the following advantage is afforded in addition to the advantage in the first embodiment. The responsiveness in bending motion of the bending section 15 in the UD direction and the LR direction differs depending on the difference in routing shape of the wires 15a and 15b in the mounting unit 16, in addition to the curved shapes of the flexible section 14 and the bending section 15 described in the first embodiment. An advantage is afforded in that, by setting the compensation values $Gff_{UD}$ and $Gff_{LR}$ by taking into account the routing shapes of these wires 15a and 15b, a decrease or variation in responsiveness in bending motion of the bending section 15 can be compensated for with still higher accuracy.

Third Embodiment

A manipulator system 300 according to a third embodiment of the present invention will now be described with reference to FIGS. 14 through 15D.

In this embodiment, differences from the above-described first and second embodiments will mainly be described, and structures in common with those in the first and second embodiments will be denoted with the same reference signs and descriptions thereof will be omitted.

Figure 14:
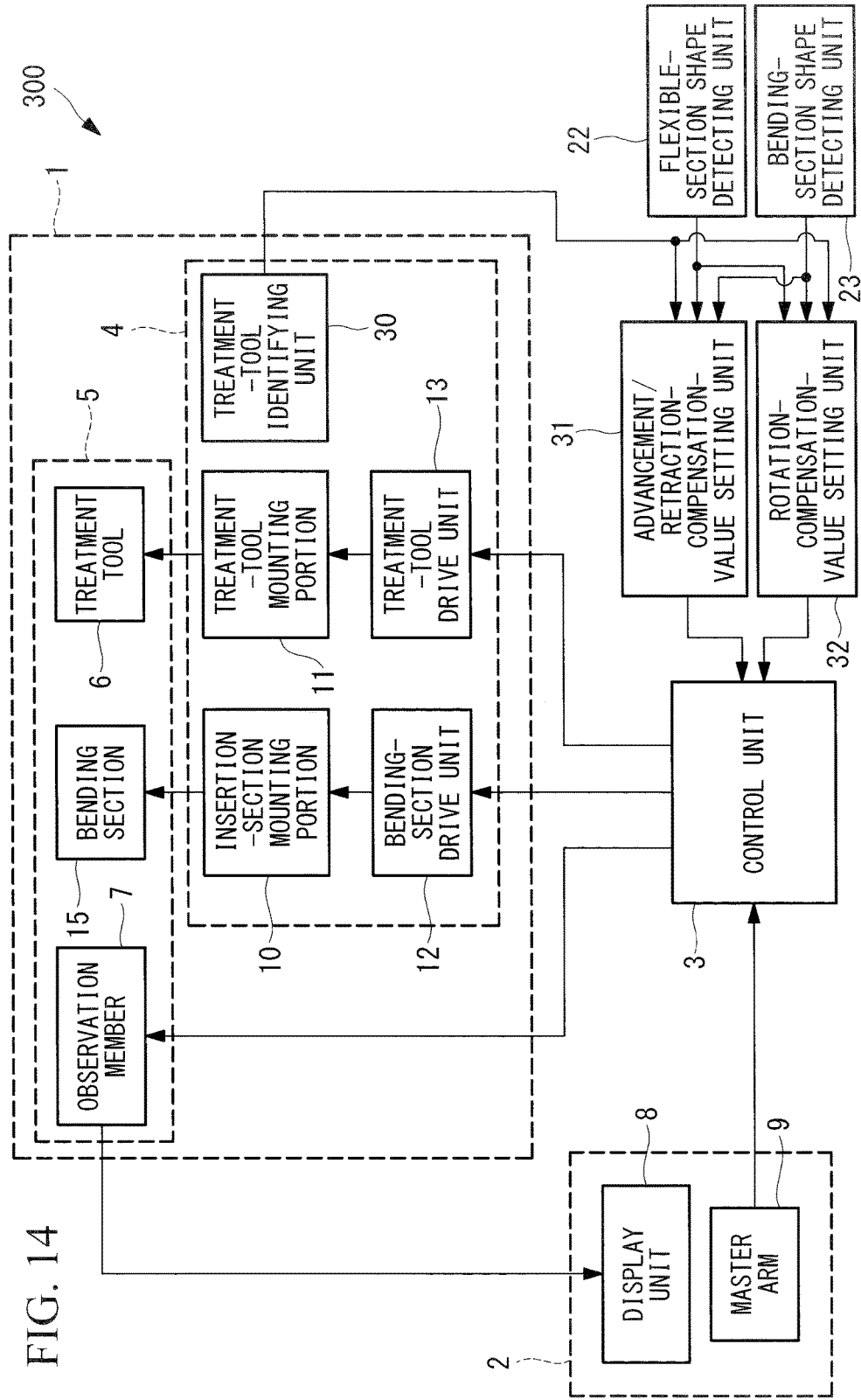
FIG. 14 is a block diagram showing the overall structure of a manipulator system according to a third embodiment of the present invention.

As shown in FIG. 14, the manipulator system 300 of this embodiment differs from the first and second embodiments mainly in that a treatment-tool identifying unit 30 is further provided and that compensation-value setting units 31 and 32 for setting the compensation values $Gff_{bf}$ and $Gff_{rot}$ for the control of the treatment-tool drive unit 13 are provided instead of the compensation-value setting units 24 and 25.

The mounting unit 20 is provided with a recording medium that stores the identification information for identifying the treatment tool 6 to which the mounting unit 20 is connected.

The treatment-tool identifying unit 30 reads out the identification information recorded on the recording medium of the mounting unit 20 mounted to the treatment-tool mounting portion 11 and transmits the read-out identification information to the compensation-value setting units 31 and 32.

The recording medium and other structures of the treatment-tool identifying unit 30 are the same as the recording medium and those of the treatment-tool identifying unit 26 described in the first embodiment.

In this embodiment, the compensation-value setting units 31 and 32 are composed of the advancement/retraction-compensation-value setting unit (compensation-value setting unit) 31 for setting the compensation value for advancement/retraction motion of the treatment tool 6 and the rotation-compensation-value setting unit (compensation-value setting unit) 32 for setting the compensation value for rotational motion of the treatment tool 6.

The advancement/retraction-compensation-value setting unit 31 sets the FF gain $Gff_{bf}$ used by the control unit 3 for FF control of advancement/retraction motion of the treatment tool 6 on the basis of expression (3) below.

$$Gff_{bf} = gff_{bf} \times \alpha_{bf}(\theta_{UD}, \theta_{LR}) \times \beta_{bf}(k) \qquad (3)$$

Here, $gff_{bf}$ is an FF gain when the flexible section 14 and the bending section 15 extend in a straight line (i.e., when $\theta_{LR} = \theta_{UD} = k = 0$), $\alpha_{bf}(\theta_{UD}, \theta_{LR})$ is a compensation factor according to the curvature angles $\theta_{UD}$ and $\theta_{LR}$ of the bending section 15, and $\beta_{bf}(k)$ is a compensation factor according to the feature quantity k of the flexible section 14. However, $\alpha_{UD}(0,0) = 1$ and $\beta_{bf}(0) = 1$.

The compensation factor $\alpha_{bf}(\theta_{UD}, \theta_{LR})$ is a proportional function or a polynomial function of the curvature angles $\theta_{UD}$ and $\theta_{LR}$ and differs depending on dynamic characteristics of the bending section 15. The compensation factor $\beta_{bf}(k)$ is a proportional function or a polynomial function of the feature quantity k and differs depending on dynamic characteristics of the flexible section 14. These compensation factors $\alpha_{bf}(\theta_{UD}, \theta_{LR})$ and $\beta_{bf}(k)$ are experimentally or theoretically determined in the same manner as the compensation factors $\alpha_{UD}(\theta_{LR})$, $\alpha_{LR}(\theta_{UD})$, and $\beta_{ff}(k)$ described in the first embodiment. Alternatively, the compensation factors $\alpha_{bf}(\theta_{UD}, \theta_{LR})$ and $\beta_{bf}(k)$ may be determined by combining a theoretical approach and an experimental approach.

In the same manner, the rotation-compensation-value setting unit 32 sets an FF gain $Gff_{rot}$ used by the control unit 3 for FF control of rotational motion of the treatment tool 6 on the basis of expression (4) below.

$$Gff_{rot} = gff_{rot} \times \alpha_{rot}(\theta_{UD}, \theta_{LR}) \times \beta_{rot}(k) \qquad (4)$$

Here, $gff_{rot}$ is an FF gain when the flexible section 14 and the bending section 15 extend in a straight line (i.e., when $\theta_{UD} = \theta_{LR} = k = 0$) $\alpha_{rot}(\theta_{UD}, \theta_{LR})$ is a compensation factor according to the curvature angles $\theta_{LR}$ and $\theta_{UD}$ of the bending section 15, and $\beta_{rot}(k)$ is a compensation factor according to the feature quantity k of the flexible section 14. However, $\alpha_{rot}(0,0) = 1$ and $\beta_{rot}(0) = 1$.

The advancement/retraction-compensation-value setting unit 31 stores a combination of the compensation factors $\alpha_{bf}(\theta_{UD}, \theta_{LR})$ and $\beta_{bf}(k)$ that correspond to identification information for the treatment tool 6 and that are set according to the dynamic characteristics (e.g., stiffness and friction factor) of each of the treatment tools 6. The advancement/retraction-compensation-value setting unit 31 selects the combination of the compensation factors $\alpha_{bf}(\theta_{UD}, \theta_{LR})$ and $\beta_{bf}(k)$ corresponding to the identification information received from the treatment-tool identifying unit 30 and calculates the FF gain $\text{Gff}_{LR}$ from expression (3) using the selected compensation factors $\alpha_{bf}(\theta_{UD}, \theta_{LR})$ and $\rho_{bf}(k)$.

The rotation-compensation-value setting unit 32 stores a combination of the compensation factors $\alpha_{rot}(\theta_{UD}, \theta_{LR})$ and $\beta_{rot}(k)$ that correspond to identification information for the treatment tool 6 and that are set according to the dynamic characteristics (e.g., stiffness and friction factor) of each of the treatment tools 6. The rotation-compensation-value setting unit 32 selects the combination of the compensation factors $\alpha_{rot}(\theta_{UD}, \theta_{LR})$ and $\beta_{rot}(k)$ corresponding to the identification information received from the treatment-tool identifying unit 30 and calculates the FF gain $\text{Gff}_{rot}$ from expression (4) using the selected compensation factors $\alpha_{rot}(\theta_{UD}, \theta_{LR})$ and $\beta_{rot}(k)$.

The control unit 3 multiplies the advancement/retraction control signal and the rotation control signal generated from the operating signal input from the master input unit 2 by the FF gains $\text{Gff}_{bf}$ and $\text{Gff}_{rot}$ obtained from expression (3) and expression (4), respectively, to amplify these control signals and then transmits the amplified control signals to the treatment-tool drive unit 13. By doing so, the treatment-tool drive unit 13 is FF-controlled.

The operation of the manipulator system 300 with this structure will now be described.

The basic procedures are the same as in the first embodiment. The manipulator system 100 of this embodiment differs from the first and second embodiments in control when the treatment tool 6 is advanced/retracted or rotated.

When the practitioner Op inputs to the master arm 9 an operation for advancing or retracting the treatment tool 6, an operating signal according to this operation is transmitted from the master arm 9 to the control unit 3. From the received operating signal, the control unit 3 generates an advancement/retraction control signal for advancement/retraction motion and a rotation control signal for rotational motion of the treatment tool 6. On the other hand, the compensation-value setting units 31 and 32 set the FF gains $\text{Gff}_{bf}$ and $\text{Gff}_{rot}$ on the basis of the curved shapes of the flexible section 14 and the bending section 15 at that time and transmit the FF gains $\text{Gff}_{bf}$ and $\text{Gff}_{rot}$ to the control unit 3. The control unit 3 transmits to the treatment-tool drive unit 13 the advancement/retraction control signal and the rotation control signal amplified by the FF gains $\text{Gff}_{bf}$ and $\text{Gff}_{rot}$ to FF-control the treatment-tool drive unit 13.

Response characteristics of the motion of the treatment tool 6 to an operation input by the practitioner Op to the master arm 9 will now be described.

Figure 15C:
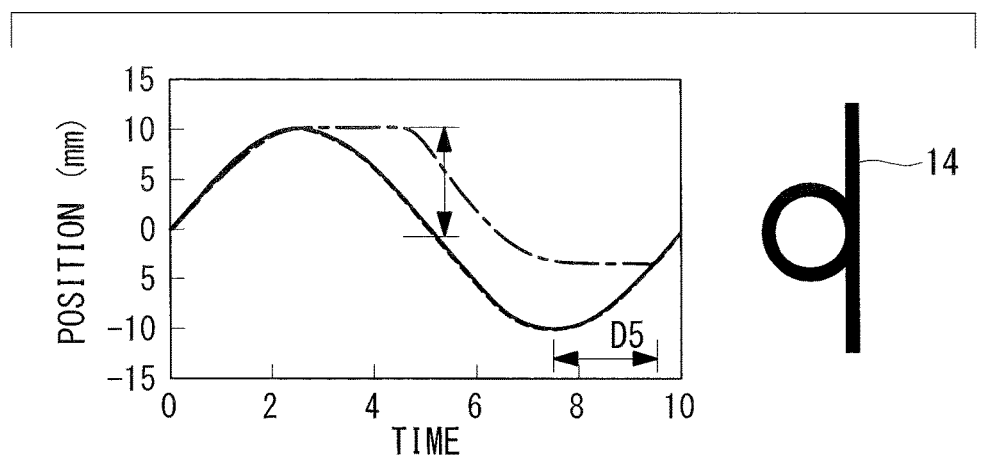
FIG. 15C is graph illustrating a response characteristic of the bending section in normal control when the flexible section is curved in another shape.

FIGS. 15A through 15D depict response characteristics of advancement/retraction motion of the treatment tool 6 to an operating signal. FIG. 15A depicts characteristics when the flexible section 14 and the bending section 15 extend in a straight line, FIG. 15B depicts characteristics when the flexible section 14 is bent 180° so as to form a semicircle 150 mm in diameter, and FIG. 15C depicts characteristics when the flexible section 14 is bent 360° so as to form a circle 150 mm in diameter. In FIGS. 15A through 15D, the solid lines indicate an operating signal generated by the master input unit 2, the broken lines indicate the position of the treatment tool 6 theoretically calculated from the output of the encoder provided in the treatment-tool drive unit 13, and the chain lines indicate the actual position of the treatment tool 6.

As shown in FIGS. 15A through 5C, during normal control (i.e., without FF control) in which the motors 13a and 13b are controlled such that the amounts of rotation of the motors 13a and 13b in the treatment-tool drive unit 13 are proportional to the amount of operation input to the master arm 9, delay times as seen in FIGS. 9A and 9B occur, and furthermore deadbands D3, D4, and D5, in which advancement/retraction motions of the treatment tool 6 do not follow the rotation of the motors 13a and 13b, exist. The delay times and the deadbands D3, D4, and D5 are even larger when the flexible section 14 is bent than when the flexible section 14 is in a straight line, demonstrating that the responsiveness in advancement/retraction motion of the treatment tool 6 to the operation input by the practitioner Op to the master arm 9 differs depending on the shape of the flexible section 14. Such a variation in responsiveness in advancement/retraction motion of the treatment tool 6 occurs for the same reason as the variation in responsiveness in bending motion of the bending section 15 described in the first embodiment.

Figure 15D:
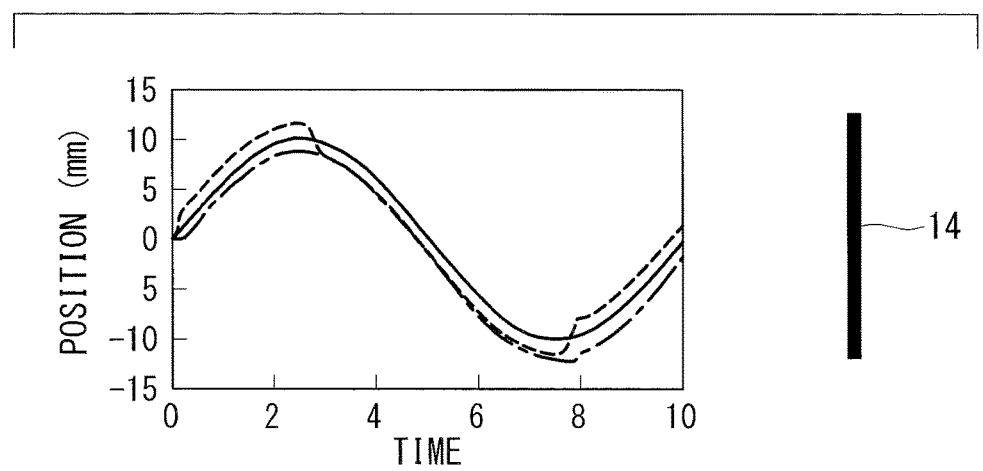
FIG. 15D is a graph illustrating a response characteristic of the bending section in FF control when the flexible section is in a straight line.

FIG. 15D illustrates a response characteristic of advancement/retraction motion of the treatment tool 6 when the treatment-tool drive unit 13 is FF-controlled in a state where the flexible section 14 is extended in a straight line, as in FIG. 15A. As is understood from FIG. 15D, the delay time and deadband are significantly reduced, and responsiveness in advancement/retraction motion of the treatment tool 6 to the operating signal is enhanced.

Similar characteristics of responsiveness can also be seen with rotational motion of the treatment tool 6. More specifically, the responsiveness in rotational motion of the treatment tool 6 to the operating signal changes depending on the curved shapes of the flexible section 14 and the bending section 15, and the responsiveness of the treatment tool 6 decreases when the flexible section 14 and the bending section 15 are bent, compared with when the flexible section 14 and the bending section 15 extend in a straight line. This decrease in responsiveness can also be reduced by FF-controlling the treatment-tool drive unit 13.

In this manner, according to this embodiment, a decrease or variation in responsiveness in motion of the treatment tool 6 dependent on differences in curved shapes of the flexible section 14 and the bending section 15 can be compensated for with high accuracy by compensating the advancement/retraction control signal and the rotation control signal for advancing/retracting and rotating the treatment tool 6 on the basis of the curved shapes of both the flexible section 14 and the bending section 15. By doing so, an advantage is afforded in that superior and constant responsiveness in advancement/retraction motion and rotational motion of the treatment tool 6 can be achieved at all times.

In this embodiment, as with the first embodiment, the compensation-value setting units 31 and 32 may set, instead of an FF gain, an FB gain used by the control unit 3 for FB control of the motors 13a and 13b, and the control unit 3 may set a friction compensation factor (offset signal) to be superimposed onto the curvature control signal.

Fourth Embodiment

A manipulator system 400 according to a fourth embodiment of the present invention will now be described with reference to FIG. 16.

In this embodiment, differences from the above-described first through third embodiments will mainly be described, and structures in common with those in the first through third embodiments will be denoted with the same reference signs and descriptions thereof will be omitted.

Figure 16:
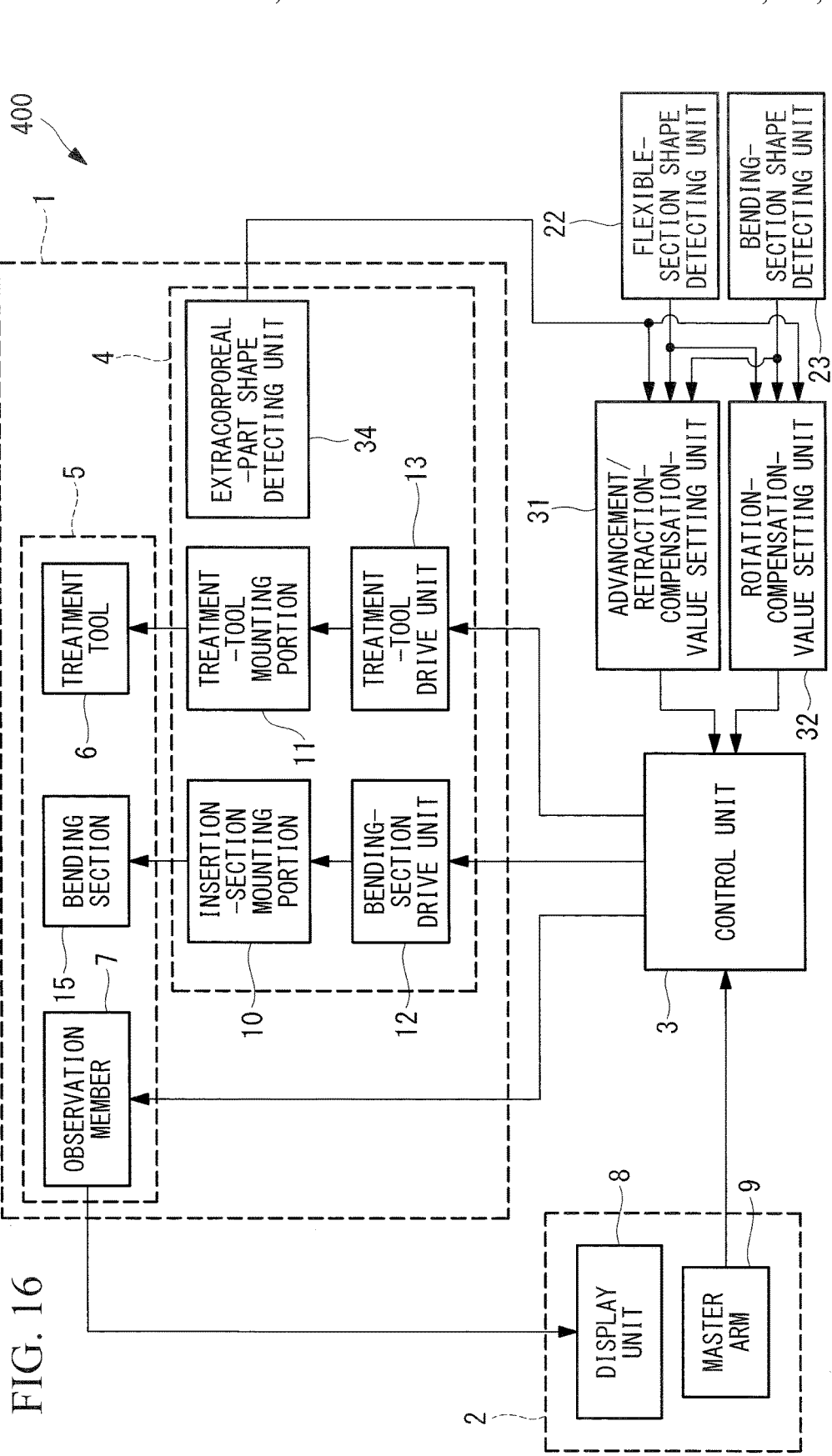
FIG. 16 is a block diagram depicting the overall structure of a manipulator system according to a fourth embodiment of the present invention.

The manipulator system 400 of this embodiment is a modification of the third embodiment and, as shown in FIG. 16, differs from the third embodiment mainly in that an extracorporeal-part shape detecting unit 34 is further provided to identify the mounting unit 20 of the treatment tool 6 inserted in the insertion section 5, thereby detecting the curved shape of the basal end portion of the main body 18 of the treatment tool 6.

The extracorporeal-part shape detecting unit 34 detects a curvature angle $\theta_{ex}$ of the portion pulled out from the treatment-tool port 17 of the main body 18 (hereinafter, this portion is referred to as an extracorporeal portion of the treatment tool 6). Depending on differences in stiffness, length, etc. of the main body 18, the routing shape of the extracorporeal portion differs for each treatment tool 6. In addition, for a structure in which a plurality of the treatment-tool mounting portions 11 are provided and a treatment-tool mounting portion 11 to which the mounting unit 20 is to be mounted is selected according to, for example, the type of the treatment tool 6 or the channel through which the treatment tool 6 is inserted, the routing shape of the extracorporeal portion of the treatment tool 6 varies because the position of the treatment-tool mounting portion 11 to which the mounting unit 20 is mounted varies.

The routing shape of the extracorporeal portion is almost constant for each combination of the treatment tool 6 and the treatment-tool mounting portion 11. Because of this, the extracorporeal-part shape detecting unit 34 stores a table in which combinations of the treatment tools 6 and the treatment-tool mounting portions 11 are associated with pre-measured curvature angles $\theta_{ex}$. The extracorporeal-part shape detecting unit 34 identifies the treatment-tool mounting portion 11 to which the mounting unit 20 is mounted, as well as the mounting unit 20, and refers to the table to obtain a curvature angle $\theta_{ex}$.

More specifically, the mounting unit 20 is provided with a recording medium that stores the identification information for identifying the mounting unit 20.

The extracorporeal-part shape detecting unit 34 reads out the identification information recorded on the recording medium of the mounting unit 20 mounted to the treatment-tool mounting portion 11 and transmits the read-out identification information to the compensation-value setting units 31 and 32.

The recording medium and other structures of the extracorporeal-part shape detecting unit 34 are the same as the recording medium and those of the treatment-tool identifying unit 26 provided in the mounting unit 20 of the treatment tool 6 described in the first embodiment.

The compensation-value setting units 31 and 32 set the FF gains $Gff_{bf}$ and $Gff_{rot}$ on the basis of expressions (5) and (6) below.

$$Gff_{bf}=gff_{bf}\times\alpha_{bf}(\theta_{UD},\theta_{LR})\times\beta_{bf}(k)\times\gamma_{bf}(\theta_{ex}) \quad (5)$$

$$Gff_{rot}=gff_{rot}\times\alpha_{rot}(\theta_{UD},\theta_{LR})\times\beta_{rot}(k)\times\gamma_{rot}(\theta_{ex}) \quad (6)$$

where $\gamma_{bf}(\theta_{ex})$ and $\gamma_{rot}(\theta_{ex})$ denote compensation factors according to the curvature angle $\theta_{ex}$. However, $\gamma_{bf}(0)=\gamma_{rot}(0)=1$.

According to the manipulator system 400 of this embodiment, the following advantage is afforded in addition to the advantage of the third embodiment. The responsiveness in advancement/retraction motion and rotational motion of the treatment tool 6 differs depending on differences in the curved shape of the extracorporeal portion of the treatment tool 6 located outside the insertion section 5, in addition to the curved shapes of the flexible section 14 and the bending section 15. An advantage is afforded in that a decrease or variation in responsiveness in advancement/retraction motion and rotational motion of the treatment tool 6 can be compensated for with still higher accuracy by setting the compensation values $Gff_{bf}$ and $Gff_{rot}$ by also taking into account the curved shape of this extracorporeal portion.

Although this embodiment has been described by way of example of the insertion section 5 having only one channel for the treatment tool 6, the insertion section 5 may have two or more channels.

In this case, it is preferable that the manipulator system 400 further include a channel-in-use detecting unit (not shown in the figure) for detecting into which channel the treatment tool 6 is inserted so that the compensation-value setting units 31 and 32 set the compensation values $Gff_{bf}$ and $Gff_{rot}$ further on the basis of the channel detected by the channel-in-use detecting unit.

If a plurality of channels are provided in the insertion section 5, the responsiveness of the treatment tool 6 may differ depending on which of the channels the treatment tool 6 is inserted into. In short, in the channel, frictional force exerted on the treatment tool 6 differs depending on the combination of the shape/material of the internal surface of the channel and the shape/material of the treatment tool 6. Furthermore, the curved shape of the treatment tool 6 when the insertion section 5 is bent differs depending on which of the channels the treatment tool 6 is inserted into.

This modification affords an advantage in that as a result of the compensation-value setting units 31 and 32 setting the compensation values $Gff_{bf}$ and $Gff_{rot}$ according to a combination of the channel and the treatment tool 6, a decrease or variation in responsiveness in motion of the treatment tool 6 can be compensated for with still higher accuracy.

Fifth Embodiment

A manipulator system 500 according to a fifth embodiment of the present invention will now be described with reference to FIG. 17.

In this embodiment, differences from the above-described first through fourth embodiments will mainly be described, and structures in common with those in the first through fourth embodiments will be denoted with the same reference signs and descriptions thereof will be omitted.

Figure 17:
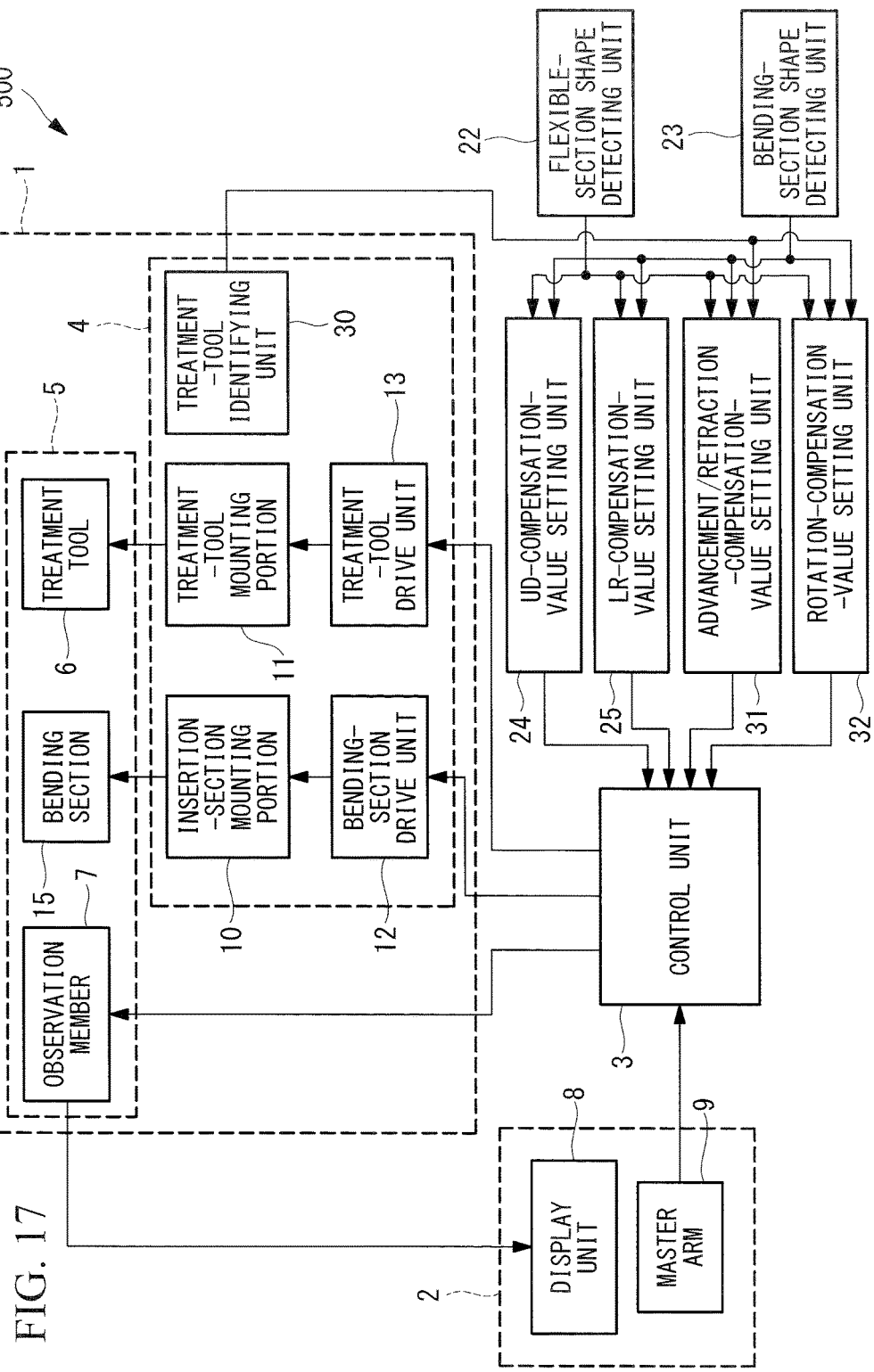
FIG. 17 is a block diagram depicting the overall structure of a manipulator system according to a fifth embodiment of the present invention.

The manipulator system 500 of this embodiment is a combination of the first embodiment and the third embodiment and includes the above-described four compensation-value setting units 24, 25, 31, and 32, as shown in FIG. 17.

As described in the first embodiment, the control unit 3 FF-controls the bending-section drive unit 12 using the FF gains $Gff_{UD}$ and $Gff_{LR}$ set by the UD-compensation-value setting unit 24 and the LR-compensation-value setting unit 25. At the same time, the control unit 3 FF-controls the treatment-tool drive unit 13 using the FF gains $Gff_{bf}$ and $Gff_{rot}$ set by the advancement/retraction-compensation-value setting unit 31 and the rotation-compensation-value setting unit 32.

This embodiment affords an advantage in that responsiveness in both bending motion of the bending section 15 and advancement/retraction motion and rotational motion of the treatment tool 6 can be compensated together according to the curved shapes of the flexible section 14 and the bending section 15.

From the above-described embodiments and modifications thereof, the following aspects of the invention are derived.

A first aspect of the present invention is a manipulator system including: a manipulator that includes an insertion section having an elongated flexible section with flexibility and a bending section provided at a distal end of the flexible section and that includes a bending-section drive unit for causing the bending section. to undergo bending motion; an operation input unit via which an operator inputs an operating instruction to the bending section; a flexible-section shape detecting unit that detects a curved shape of the flexible section; a bending-section shape detecting unit that detects a curved shape of the bending section; a control unit that generates a curvature control signal for driving the bending-section drive unit according to the operating instruction input via the operation input unit; and a compensation-value setting unit that sets a compensation value for the curvature control signal on the basis of the curved shape of the flexible section detected by the flexible-section shape detecting unit and the curved shape of the bending section detected by the bending-section shape detecting unit, wherein the control unit corrects the curvature control signal with the compensation value set by the compensation-value setting unit and transmits the corrected curvature control signal to the bending-section drive unit.

According to this aspect, when the operator inputs the operating instruction via the operation input unit, the control unit corrects the curvature control signal generated from this operating instruction using the compensation value set by the compensation-value setting unit and then transmits it to the bending-section drive unit, thereby causing the bending section to undergo a bending motion corresponding to the operating instruction. By doing so, the bending section of the insertion section disposed, for example, in the body can be remotely operated using the operation input unit disposed outside the body.

In this case, responsiveness in bending motion of the bending section to the operating signal depends on the curved shapes of both the flexible section and the bending section. The compensation value is set on the basis of the curved shapes of both the flexible section and the bending section detected by the flexible-section shape detecting unit and the bending-section shape detecting unit. As a result, a decrease or variation in responsiveness of the bending section can be compensated for with high accuracy to achieve superior and constant responsiveness at all times.

In the above-described first aspect, the manipulator may include a treatment tool that is inserted in the insertion section along a longitudinal direction thereof, and the manipulator system further may comprise a treatment-tool identifying unit that identifies whether the treatment tool is present or absent in the insertion section and, if the treatment tool is present in the insertion section, the treatment tool, and the compensation-value setting unit may set the compensation value further on the basis of presence/absence of the treatment tool identified by the treatment-tool identifying unit and, if the treatment tool is present in the insertion section, a dynamic characteristic of the treatment tool identified by the treatment-tool identifying unit.

In this case, the responsiveness of the bending section also depends on whether or not the treatment tool is present in the insertion section and the dynamic characteristics of that treatment tool. Therefore, by also reflecting whether or not the treatment tool is present in the insertion section and dynamic characteristics of the treatment tool in the compensation value, the decrease or variation in responsiveness of the bending section can be compensated for with still higher accuracy.

In the above-described aspect, the manipulator may include a linear member that connects the bending section and the bending-section drive unit via the flexible section and transmits to the bending section a driving force generated by the bending-section drive unit, and a path for setting a route of the linear member in the insertion section may be provided in the insertion section.

By doing so, variation in friction or slackness arising in the linear member, which serves as a factor affecting the variation in responsiveness of the bending section, can be reduced, thereby compensating for the decrease or variation in responsiveness of the bending section with still higher accuracy.

In the above-described first aspect, the manipulator may include a linear member that connects the bending section and the bending-section drive unit via the flexible section and transmits to the bending section a driving force generated by the bending-section drive unit, and the manipulator system further may comprise an extracorporeal-part shape detecting unit that detects a curved shape of a basal end portion of the linear member pulled out of the insertion section, and the compensation-value setting unit may set the compensation value further on the basis of the curved shape of the basal end portion of the linear member detected by the extracorporeal-part shape detecting unit.

In this case, the responsiveness of the bending section also depends on the curved shape of the basal end portion of the linear member located outside the insertion section. Therefore, by also reflecting the curved shape of the basal end portion of the linear member outside the insertion section in the compensation value, the decrease or variation in responsiveness of the bending section can be compensated for with still higher accuracy.

In the above-described first aspect, the control unit may feedforward-control or feedback-control the bending-section drive unit, and the compensation-value setting unit may set, as the compensation value, a gain used by the control unit for the feedforward or feedback control.

By doing so, the decrease or variation in responsiveness of the bending section can be compensated for using a simple control method.

In the above-described first aspect, the control unit may transmit to the bending-section drive unit the curvature control signal having an offset signal superimposed thereon, and the compensation-value setting unit may set, as the compensation value, the offset signal the sign of which is reversed when the direction of the bending motion of the bending section changes to a reverse direction.

By doing so, a backlash arising when the direction of the bending motion of the bending section is reversed can be eliminated effectively.

A second aspect of the present invention is a manipulator system including: a manipulator having an insertion section that includes an elongated flexible section with flexibility and that includes a bending section provided at a distal end of the flexible section, a treatment tool inserted in the insertion section along a longitudinal direction thereof, and a treatment-tool drive unit that causes the treatment tool to undergo advancement/retraction motion and rotational motion in the insertion section; an operation input unit via which an operator inputs an operating instruction to the treatment tool; a flexible-section shape detecting unit that detects a curved shape of the flexible section; a bending-section shape detecting unit that detects a curved shape of the bending section; a control unit that generates an advancement/retraction control signal and a rotation control signal for driving the treatment-tool drive unit according to the operating instruction input via the operation input unit; and a compensation-value setting unit that sets a compensation value for the advancement/retraction control signal and the rotation control signal on the basis of the curved shape of the flexible section detected by the flexible-section shape detecting unit and the curved shape of the bending section detected by the bending-section shape detecting unit, wherein the control unit corrects the advancement/retraction control signal and the rotation control signal with the compensation values set by the compensation-value setting unit and transmits the advancement/retraction control signal and the rotation control signal to the treatment-tool drive unit.

According to this aspect, when the operator inputs the operating instruction via the operation input unit, the control unit corrects the advancement/retraction control signal and the rotation control signal generated from this operating instruction, using the compensation value set by the compensation-value setting unit, and then transmits them to the treatment-tool drive unit, thereby allowing the treatment tool to perform advancement/retraction motion and rotational motion corresponding to the operating instruction. Because of this, for example, the treatment tool disposed in the body via the insertion section can be remotely operated using the operation input unit disposed outside the body.

In this case, the responsiveness in advancement/retraction motion and rotational motion of the treatment tool to an operating signal depends on the curved shapes of both the flexible section and the bending section. The compensation value is set on the basis of the curved shapes of both the flexible section and the bending section detected by the flexible-section shape detecting unit and the bending-section shape detecting unit. Because of this, a decrease or variation in responsiveness of the treatment tool can be compensated for with high accuracy, thereby achieving superior and constant responsiveness at all times.

In the above-described second aspect, the manipulator system may further include: a treatment-tool identifying unit that identifies the treatment tool in the insertion section, wherein the compensation-value setting unit may set each of the compensation values further on the basis of a dynamic characteristic of the treatment tool identified by the treatment-tool identifying unit.

In this case, the responsiveness of the treatment tool depends on the dynamic characteristics of that treatment tool. Therefore, by also reflecting the dynamic characteristics of the treatment tool in the compensation value, the decrease and variation in responsiveness of the treatment tool can be compensated for with still higher accuracy.

In the above-described second aspect, the manipulator system may further include: an extracorporeal-part shape detecting unit that detects the curved shape of a basal end portion of the treatment tool pulled out of the insertion section, wherein the compensation-value setting unit may set each of the compensation values further on the basis of the curved shape of the basal end portion of the treatment tool detected by the extracorporeal-part shape detecting unit.

In this case, responsiveness of the treatment tool also depends on the curved shape of the basal end portion located outside the insertion section. Therefore, also by reflecting on the compensation value the curved shape of the basal end portion of the treatment tool located outside the insertion section, the decrease or variation in responsiveness of the treatment tool can be compensated for with still high accuracy.

In the above-described second aspect, the insertion section may be provided with a plurality of channels that penetrate therethrough in the longitudinal direction and into which the treatment tool is inserted, and the manipulator system further may comprise a channel-in-use detecting unit that detects, from among the plurality of channels, a channel into which the treatment tool is inserted may be provided, and the compensation-value setting unit may set each of the compensation values further on the basis of the channel detected by the channel-in-use detecting unit.

In this case, the responsiveness of the treatment tool also depends on the characteristics thereof, such as the position in the insertion section or the inner diameter of the channel in which the treatment tool is disposed. Therefore, by also reflecting the channel in which the treatment tool is disposed in the compensation value, the decrease or variation in responsiveness of the treatment tool can be compensated for with still higher accuracy.

In the above-described second aspect, the control unit may feedforward-control or feedback-control the treatment-tool drive unit, and the compensation-value setting unit may set, as the compensation value, a gain used by the control unit for the feedforward or feedback control.

In the above-described second aspect, the control unit may transmit to the treatment-tool drive unit the advancement/retraction control signal and the rotation control signal having an offset signal superimposed thereon, and, the compensation-value setting unit may set, as the compensation values, the offset signal the sign of which is reversed when the direction of the advancement/retraction motion or the rotational motion of the treatment tool changes to a reverse direction.

REFERENCE SIGNS LIST 1 slave manipulator (manipulator)
2 master input unit (operation input unit)
3 control unit
4 slave arm
5 insertion section
6 treatment tool
7 observation member
8 display unit
9 master arm
10 insertion-section mounting portion
11 treatment tool mounting portion
12 bending-section drive unit
13 treatment-tool drive unit
13a rotation motor
13b linear motor
14 flexible section
15 bending section
15a, 15b wire (linear member)
16, 20 mounting unit
17 port for treatment tool
18 main body
19 treatment part
20a pulley
20b stage
22 flexible-section shape detecting unit
23 bending-section shape detecting unit
24 UD-compensation-value setting unit (compensation-value setting unit)

25 LR-compensation-value setting unit (compensation-value setting unit)
26, 30 treatment-tool identifying unit
27 path
29, 34 extracorporeal-part shape detecting unit
31 advancement/retraction-compensation-value setting unit (compensation-value setting unit)
32 rotation-compensation-value setting unit (compensation-value setting unit)
80 operating table
100, 200, 300, 400, 500 manipulator system
X colon
Op practitioner (operator)

The invention claimed is:

1. A manipulator system comprising:
a manipulator that includes an insertion section having an elongated flexible section with flexibility and a bending section provided at a distal end of the flexible section and that includes a bending-section drive unit for causing the bending section to undergo bending motion;
an operation input unit via which an operator inputs an operating instruction to the bending section;
a flexible-section shape detecting unit that detects a curved shape of the flexible section;
a bending-section shape detecting unit that detects a curved shape of the bending section;
a control unit that generates a curvature control signal for driving the bending-section drive unit according to the operating instruction input via the operation input unit; and
a compensation-value setting unit that sets a compensation value for the curvature control signal on the basis of the curved shape of the flexible section detected by the flexible-section shape detecting unit and the curved shape of the bending section detected by the bending-section shape detecting unit,
wherein the control unit corrects the curvature control signal with the compensation value set by the compensation-value setting unit and transmits the corrected curvature control signal to the bending-section drive unit.

2. The manipulator system according to claim 1,
wherein the manipulator includes a treatment tool that is inserted in the insertion section along a longitudinal direction thereof, and
the manipulator system further comprises a treatment-tool identifying unit that identifies whether the treatment tool is present or absent in the insertion section and, if the treatment tool is present in the insertion section, the treatment tool, and
the compensation-value setting unit sets the compensation value further on the basis of presence/absence of the treatment tool identified by the treatment-tool identifying unit and, if the treatment tool is present in the insertion section, a dynamic characteristic of the treatment tool identified by the treatment-tool identifying unit.

3. The manipulator system according to claim 1,
wherein the manipulator includes a linear member that connects the bending section and the bending-section drive unit via the flexible section and transmits to the bending section a driving force generated by the bending-section drive unit, and
a path for setting a route of the linear member in the insertion section is provided in the insertion section.

4. The manipulator system according to claim 1,
wherein the manipulator includes a linear member that connects the bending section and the bending-section drive unit via the flexible section and transmits to the bending section a driving force generated by the bending-section drive unit, and
the manipulator system further comprises an extracorporeal-part shape detecting unit that detects a curved shape of a basal end portion of the linear member pulled out of the insertion section, and
the compensation-value setting unit sets the compensation value further on the basis of the curved shape of the basal end portion of the linear member detected by the extracorporeal-part shape detecting unit.

5. The manipulator system according to claim 1,
wherein the control unit feedforward-controls the bending-section drive unit, and
the compensation-value setting unit sets, as the compensation value, a gain used by the control unit for the feedforward control.

6. The manipulator system according to claim 1,
wherein the control unit feedback-controls the bending-section drive unit, and
the compensation-value setting unit sets, as the compensation value, a gain used by the control unit for the feedback control.

7. The manipulator system according to claim 1,
wherein the control unit transmits to the bending-section drive unit the curvature control signal having an offset signal superimposed thereon, and
the compensation-value setting unit sets, as the compensation value, the offset signal the sign of which is reversed when the direction of the bending motion of the bending section changes to a reverse direction.

8. A manipulator system comprising:
a manipulator having an insertion section that includes an elongated flexible section with flexibility and that includes a bending section provided at a distal end of the flexible section, a treatment tool inserted in the insertion section along a longitudinal direction thereof, and a treatment-tool drive unit that causes the treatment tool to undergo advancement/retraction motion and rotational motion in the insertion section;
an operation input unit via which an operator inputs an operating instruction to the treatment tool;
a flexible-section shape detecting unit that detects a curved shape of the flexible section;
a bending-section shape detecting unit that detects a curved shape of the bending section;
a control unit that generates an advancement/retraction control signal and a rotation control signal for driving the treatment-tool drive unit according to the operating instruction input via the operation input unit; and
a compensation-value setting unit that sets a compensation value for each of the advancement/retraction control signal and the rotation control signal on the basis of the curved shape of the flexible section detected by the flexible-section shape detecting unit and the curved shape of the bending section detected by the bending-section shape detecting unit,
wherein the control unit corrects the advancement/retraction control signal and the rotation control signal with the compensation values set by the compensation-value setting unit and transmits the advancement/retraction control signal and the rotation control signal to the treatment-tool drive unit.

9. The manipulator system according to claim 8, further comprising:
a treatment-tool identifying unit that identifies the treatment tool in the insertion section,
wherein the compensation-value setting unit sets each of the compensation values further on the basis of a dynamic characteristic of the treatment tool identified by the treatment-tool identifying unit.

10. The manipulator system according to claim 8, further comprising:
an extracorporeal-part shape detecting unit that detects the curved shape of a basal end portion of the treatment tool pulled out of the insertion section,
wherein the compensation-value setting unit sets each of the compensation values further on the basis of the curved shape of the basal end portion of the treatment tool detected by the extracorporeal-part shape detecting unit.

11. The manipulator system according to claim 8,
wherein the insertion section is provided with a plurality of channels that penetrate therethrough in the longitudinal direction and into which the treatment tool is inserted, and
the manipulator system further comprises a channel-in-use detecting unit that detects, from among the plurality of channels, a channel into which the treatment tool is inserted is provided, and
the compensation-value setting unit sets each of the compensation values further on the basis of the channel detected by the channel-in-use detecting unit.

12. The manipulator system according to claim 8,
wherein the control unit feedforward-controls the treatment-tool drive unit, and
the compensation-value setting unit sets, as the compensation value, a gain used by the control unit for the feedforward control.

13. The manipulator system according to claim 8,
wherein the control unit feedback-controls the treatment-tool drive unit, and
the compensation-value setting unit sets, as the compensation value, a gain used by the control unit for feedback control.

14. The manipulator system according to claim 8,
wherein the control unit transmits to the treatment-tool drive unit the advancement/retraction control signal and the rotation control signal having an offset signal superimposed thereon, and,
the compensation-value setting unit sets, as each of the compensation values, the offset signal the sign of which is reversed when the direction of the advancement/retraction motion or the rotational motion of the treatment tool changes to a reverse direction.

* * * * *